US 8,961,904 B2

(12) United States Patent
Xia et al.

(10) Patent No.: US 8,961,904 B2
(45) Date of Patent: Feb. 24, 2015

(54) MICROFLUIDIC CHIP

(71) Applicant: Premium Genetics (UK) Ltd., Nantwich (GB)

(72) Inventors: Zheng Xia, Middleton, WI (US); Yu Zhou, Middleton, WI (US); John Larsen, Madison, WI (US); Guocheng Shao, Madison, WI (US); Shane Peterson, Madison, WI (US); Marjorie Faust, Waunakee, WI (US)

(73) Assignee: Premium Genetics (UK) Ltd., Nantwich (GB)

( * ) Notice: Subject to any disclaimer, the term of this patent is extended or adjusted under 35 U.S.C. 154(b) by 0 days.

(21) Appl. No.: 13/943,322

(22) Filed: Jul. 16, 2013

(65) Prior Publication Data

US 2015/0024373 A1    Jan. 22, 2015

(51) Int. Cl.
| | | |
|---|---|---|
| *B01D 43/00* | (2006.01) | |
| *B01L 3/00* | (2006.01) | |
| *F04B 43/09* | (2006.01) | |

(52) U.S. Cl.
CPC ... *B01L 3/502776* (2013.01); *B01L 2200/0636* (2013.01); *F04B 43/095* (2013.01); *B01L 2300/0864* (2013.01); *B01L 2400/0475* (2013.01)
USPC ....... 422/505; 422/68.1; 422/503; 435/287.3; 435/287.6; 417/413.2

(58) Field of Classification Search
None
See application file for complete search history.

(56) References Cited

U.S. PATENT DOCUMENTS

| | | | |
|---|---|---|---|
| 8,080,422 B2 | 12/2011 | Neas et al. | |
| 8,563,325 B1 * | 10/2013 | Bartsch et al. | ............... 436/180 |
| 2004/0043506 A1 | 3/2004 | Haussecker et al. | |

(Continued)

FOREIGN PATENT DOCUMENTS

| | | |
|---|---|---|
| WO | WO 2006/119806 | 11/2006 |
| WO | WO 2012/112641 | 8/2012 |
| WO | WO 2013/018273 | 2/2013 |

OTHER PUBLICATIONS

Fulwyler, Mack J., "Hydrodynamic orientation of cells" The Journal of Histochemistry and Cytochemistry, vol. 25, No. 7, pp. 781-783, 1977.

(Continued)

*Primary Examiner* — Jill Warden
*Assistant Examiner* — Timothy G Kingan
(74) *Attorney, Agent, or Firm* — Jean C. Edwards, Esq.; Edwards Neils PLLC

(57) ABSTRACT

A microfluidic chip orients and isolates components in a sample fluid mixture by two-step focusing, where sheath fluids compress the sample fluid mixture in a sample input channel in one direction, such that the sample fluid mixture becomes a narrower stream bounded by the sheath fluids, and by having the sheath fluids compress the sample fluid mixture in a second direction further downstream, such that the components are compressed and oriented in a selected direction to pass through an interrogation chamber in single file formation for identification and separation by various methods. The isolation mechanism utilizes external, stacked piezoelectric actuator assemblies disposed on a microfluidic chip holder, or piezoelectric actuator assemblies on-chip, so that the actuator assemblies are triggered by an electronic signal to actuate jet chambers on either side of the sample input channel, to jet selected components in the sample input channel into one of the output channels.

37 Claims, 12 Drawing Sheets

(56) References Cited

U.S. PATENT DOCUMENTS

| | | |
|---|---|---|
| 2004/0144648 A1 | 7/2004 | Jacobson et al. |
| 2004/0161772 A1* | 8/2004 | Bohm et al. ............... 435/6 |
| 2006/0170912 A1* | 8/2006 | Mueth et al. ............. 356/244 |
| 2007/0009386 A1* | 1/2007 | Padmanabhan et al. ..... 422/68.1 |
| 2007/0114172 A1 | 5/2007 | Mueth et al. |
| 2007/0128082 A1 | 6/2007 | Yang et al. |
| 2008/0166188 A1 | 7/2008 | Gilbert et al. |
| 2008/0299013 A1 | 12/2008 | Trieu et al. |
| 2009/0042241 A1 | 2/2009 | Yu-Chong et al. |
| 2009/0051912 A1 | 2/2009 | Salazar et al. |
| 2010/0079516 A1 | 4/2010 | Nakazawa |
| 2011/0003303 A1 | 1/2011 | Pagano et al. |
| 2012/0028366 A1* | 2/2012 | Krager et al. ............ 436/172 |
| 2012/0138152 A1* | 6/2012 | Villarruel et al. ............ 137/1 |
| 2012/0225475 A1 | 9/2012 | Wagner et al. |
| 2012/0273054 A1* | 11/2012 | Lou et al. ................ 137/13 |
| 2012/0307244 A1 | 12/2012 | Sharpe et al. |

OTHER PUBLICATIONS

Kachel, V., Kordwig, E., and Glossner, E., "Uniform lateral orientation, caused by flow forces, of flat particles in flow-through systems" The Journal of Histochemistry and Cytochemistry, vol. 25, No. 7, pp. 774-780, 1977.

International Search Report and Written Opinion issued on Mar. 7, 2014 in connection with PCT/US2013/050669 which is related to the present application.

Alexey Khodjakov et al.; "Views and Reviews A Synergy of Technologies Combining Laser Micorsurgery with Green Fluorescent Protein . . . "; Cytoskeleton; 1997; pp. 331-317; vol. 38.

Hossein Bazyar et al.; "Compact 151W green laser with U-type resonator for prostate surgery"; Optics & Laser Technology; Apr. 27, 2013; pp. 237-241; vol. 47.

International Search Report and Written Opinion, issued on Nov. 19, 2014 in related International Patent Application No. PCT/IB2014/001425.

* cited by examiner

MICROFLUIDIC CHIP

The present invention relates to a microfluidic chip design which is used to isolate particles or cellular materials into various components and fractions, using laminar flows.

BACKGROUND OF THE INVENTION

1. Field of the Invention

The present invention relates to a microfluidic chip design which is used to isolate particles or cellular materials into various components and fractions, using laminar flows.

2. Description of the Related Art

In the separation of various particles or cellular materials—for example, the separation of sperm into viable and motile sperm from non-viable or non-motile sperm, or separation by gender—the process is often a time-consuming task, with severe volume restrictions. Thus, current separation techniques cannot, for example, produce the desired yield, or process volumes of cellular materials in a timely fashion.

Thus, there is needed a separation technique and apparatus which is continuous, has high throughput, provides time saving, and which causes negligible or minimal damage to the various components of the separation. In addition, such an apparatus and method should have further applicability to biological and medical areas, not just in sperm sorting, but in the separation of blood and other cellular materials, including viral, cell organelle, globular structures, colloidal suspensions, and other biological materials.

SUMMARY OF THE INVENTION

The present invention relates to a microfluidic chip system, which includes a microfluidic chip loaded on a microfluidic chip cassette which is mounted on a microfluidic chip holder.

In one embodiment, the microfluidic chip includes a plurality of layers in which are disposed a plurality of channels including: a sample input channel into which a sample fluid mixture of components to be isolated is inputted; a first plurality of sheath fluid channels into which sheath fluids are inputted, the first plurality of sheath fluid channels which intersect the sample input channel at a first intersection, such that the sheath fluids compress the sample fluid mixture on at least two sides, such that the sample fluid mixture becomes a relatively smaller, narrower stream, bounded by the sheath fluids, while maintaining laminar flow in the sample input channel; a second plurality of sheath fluid channels, substantially of the same dimensions as the first plurality of sheath fluid channels, into which sheath fluids are inputted, the second plurality of sheath fluid channels which intersect the sample input channel at a second intersection downstream from the first intersection, in a second direction substantially 90 degrees above and below the sample input channel, such that the sheath fluids from the second plurality of sheath fluid channels compress the sample fluid mixture, such that the components in the sample fluid mixture are compressed and oriented in a predetermined direction, while still maintaining laminar flow in the sample input channel; and a plurality of output channels stemming from the sample input channel, the plurality of output channels which removes the components and the sheath fluids from the microfluidic chip.

In one embodiment, the microfluidic chip includes an interrogation apparatus which interrogates and identifies said components in said sample fluid mixture in said sample input channel, in an interrogation chamber disposed downstream from said second intersection.

In one embodiment, the microfluidic chip includes an isolating mechanism which isolates selected of said components in said sample fluid mixture downstream from said interrogation chamber, by displacing a trajectory of a stream of said sample fluid mixture in said sample input channel, and pushing said selected components in said displaced stream of sample fluid mixture into one of said plurality of output channels which lead from said interrogation chamber.

In one embodiment, the microfluidic chip further includes at least one jet chamber containing sheath fluids introduced into said jet chamber by at least one air vent; and at least one jet channel which is connected to said at least one jet chamber, said at least one jet channel which enters said sample input channel to said interrogation chamber.

In one embodiment, the isolating mechanism includes at least one piezoelectric actuator assembly disposed on at least one side of said sample input channel.

In one embodiment, the piezoelectric actuator assembly is an external, stacked piezoelectric actuator assembly.

In one embodiment, the microfluidic chip further includes a diaphragm which covers each said jet chamber; and wherein said external, stacked piezoelectric actuator assembly aligns with and displaces said diaphragm, to drive said sheath fluids in said jet chamber into said sample input channel, to displace said trajectory of said stream of said sample fluid mixture in said sample input channel into one of said plurality of output channels.

In one embodiment, the external, stacked piezoelectric actuator assembly is disposed in a microfluidic chip holder.

In one embodiment, the microfluidic chip further includes an electronic circuit connected to the piezoelectric actuator assembly, the electronic circuit which amplifies an electronic signal generated by a resistance force from the piezoelectric actuator being in contact with the diaphragm.

In one embodiment, an electric signal from the piezoelectric film shows how much strain is generated by the external, stacked piezoelectric actuator assembly.

In one embodiment, an indicator of contact is turned on automatically when contact between the piezoelectric actuator and the diaphragm is made.

In one embodiment, when sensing of the contact is made, the electronic signal exceeds a set threshold, and the piezoelectric actuator assembly compresses the jet chamber to jet sheath fluids from the jet chamber into the sample fluid channel.

In one embodiment, the indicator of contact includes a light, a sound, a haptic, or any combination thereof.

In one embodiment, the piezoelectric actuator assembly includes a flexible diaphragm which covers said jet chamber; and a piezoelectric material bonded on a top surface of said diaphragm by an adhering mechanism.

In one embodiment, when voltage is applied across electrodes of the piezoelectric actuator assembly, the flexible diaphragm bends into the jet chamber and squeezes the sheath fluids from the jet chamber into the sample input channel to deflect the selected components into one of the plurality of output channels.

In one embodiment, the jet channel is tapered when it connects to the sample input channel.

In one embodiment, the microfluidic chip further includes a plurality of outputs disposed at ends of said plurality of output channels.

In one embodiment, the plurality of output channels increase in dimension from the sample input channel.

In one embodiment, the microfluidic chip further includes a plurality of notches disposed at a bottom edge of the microfluidic chip to isolate the plurality of outputs.

In one embodiment, the sample input channel and the plurality of sheath channels are disposed in one or more planes of the microfluidic chip.

In one embodiment, the sample input channel and the plurality of sheath channels are disposed in one or more structural layers, or in-between structural layers of the microfluidic chip.

In one embodiment, at least one of the plurality of sheath channels is disposed in a different plane than a plane in which the sample input channel is disposed.

In one embodiment, at least one of the plurality of sheath channels is disposed in a different structural layer than a structural layer in which the sample input channel is disposed.

In one embodiment, the sample input channel tapers at an entry point into the first intersection with said plurality of sheath channels.

In one embodiment, the sample input channel tapers into said interrogation chamber.

In one embodiment, the plurality of sheath fluid channels taper at entry points into the sample input channel at least one of the first intersection or the second intersection.

In one embodiment, the interrogation chamber includes an opening cut through the structural layers in the microfluidic chip; and a top window is configured to receive a first covering in an opening in at least one layer of the structural layers; and a bottom window is configured to receive a second covering in an opening in at least one layer of the structural layers.

In one embodiment, the interrogation chamber includes an opening cut through the planes in the microfluidic chip; and a top window is configured to receive a first covering in an opening in at least one plane of the planes of the microfluidic chip; and a bottom window is configured to receive a second covering in an opening in at least one plane of the planes of the microfluidic chip.

In one embodiment, the interrogation apparatus includes a light source configured to emit a beam through the first covering, to illuminate and excite the components in said sample fluid mixture; and wherein emitted light induced by the beam passes through said second covering and is received by an objective lens.

In one embodiment, the interrogation apparatus includes a light source configured to emit a beam through structural layers of the microfluidic chip, to illuminate and excite the components in the sample fluid mixture; and wherein emitted light induced by the beam is received by an objective lens.

In one embodiment, the interrogation apparatus includes a light source configured to emit a beam through the planes of the microfluidic chip, to illuminate and excite said components in said sample fluid mixture; and wherein emitted light induced by said beam is received by an objective lens.

In one embodiment, the emitted light received by the objective lens is converted into an electronic signal which triggers said piezoelectric actuator assembly.

In one embodiment, one of the sample fluid mixture or the sheath fluids is pumped into the microfluidic chip by a pumping apparatus.

In one embodiment, the external tubing communicates fluids to the microfluidic chip.

In one embodiment, the components are cells.

In one embodiment, wherein the cells to be isolated include at least one of viable and motile sperm from non-viable or non-motile sperm; sperm isolated by gender and other sex sorting variations; stem cells isolated from cells in a population; one or more labeled cells isolated from un-labeled cells including sperm cells; cells, including sperm cells, distinguished by desirable or undesirable traits; genes isolated in nuclear DNA according to a specified characteristic; cells isolated based on surface markers; cells isolated based on membrane integrity or viability; cells isolated based on potential or predicted reproductive status; cells isolated based on an ability to survive freezing; cells isolated from contaminants or debris; healthy cells isolated from damaged cells; red blood cells isolated from white blood cells and platelets in a plasma mixture; or any cells isolated from any other cellular components into corresponding fractions.

In one embodiment, the isolated components are moved into one of the plurality of output channels, and unselected components flow out through another of the plurality of output channels.

In one embodiment, the microfluidic chip further includes a computer which controls the pumping of one of the sample fluid mixture or the sheath fluids into the microfluidic chip.

In one embodiment, the microfluidic chip further includes a computer which displays the components in a field of view acquired by a CCD camera disposed over the opening in the microfluidic chip.

In one embodiment, the microfluidic chip system, includes: a microfluidic chip loaded on a microfluidic chip cassette which is mounted on a microfluidic chip holder, the microfluidic chip having a sample input for introducing sample fluid into the microfluidic chip, and sheath inputs for introducing sheath fluid into the microfluidic chip; and a pumping mechanism which pumps said sample fluid from a reservoir into the sample input of the microfluidic chip, and pumps the sheath fluids into the sheath inputs of the microfluidic chip.

In one embodiment, a method of orienting and isolating components in a fluid mixture, includes: inputting a sample fluid mixture containing components into a sample input channel of a microfluidic chip; inputting sheath fluids into a plurality of first sheath fluid channels of the microfluidic chip, the sheath fluids from the first sheath fluid channels which join the sample fluid mixture in the sample input channel at a first intersection of the plurality of first sheath fluid channels and the sample input channel; wherein the sheath fluids from the first sheath fluid channels compress the sample fluid mixture in one direction in the sample input channel to focus the components in the sample fluid mixture around a center of the sample input channel; and inputting sheath fluids into a plurality of second sheath fluid channels of the microfluidic chip, the sheath fluids from the plurality of second sheath channels which join the sample fluid mixture in the sample input channel at a second intersection of the plurality of second sheath fluid channels and the sample input channel, downstream from the first intersection; wherein the sheath fluids from the plurality of second sheath fluid channels further compress the sample fluid mixture at the second intersection, in a second direction, such that the components are focused and aligned in a center of the sample input channel by both width and depth as the components flow through the sample input channel; and wherein the sheath fluids act on the components to compress and orient the components in a selected direction as the components flow through the sample fluid channel.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The objects, features and advantages of the present invention will be more readily appreciated upon reference to the following disclosure when considered in conjunction with the accompanying drawings, in which.

DETAILED DESCRIPTION OF THE INVENTION

Figure 1:
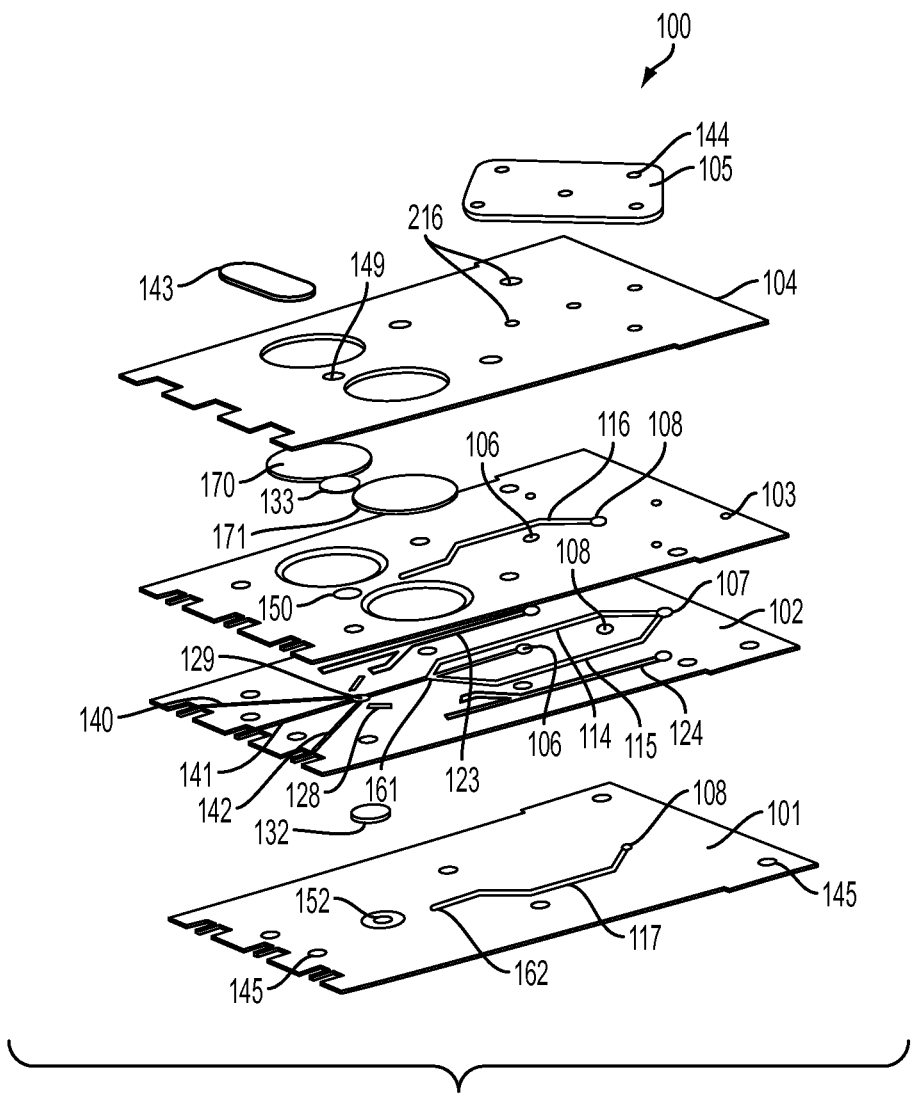
FIG. 1 shows an exploded perspective view of an illustrative embodiment of a microfluidic chip according to one embodiment consistent with the present invention.

Before turning to the figures, which illustrate the illustrative embodiments in detail, it should be understood that the present disclosure is not limited to the details or methodology set forth in the description or illustrated in the figures. It should also be understood that the terminology is for the purpose of description only and should not be regarded as limiting. An effort has been made to use the same or like reference numbers throughout the drawings to refer to the same or like parts.

The present disclosure relates to a microfluidic chip design, which is used to isolate particles or cellular materials, such as sperm, and other particles or cells, into various components and fractions, using laminar flows.

The various embodiments of the present invention provide for isolating components in a mixture, such as, for example: isolating viable and motile sperm from non-viable or non-motile sperm; isolating sperm by gender, and other sex sorting variations; isolating stems cells from cells in a population; isolating one or more labeled cells from un-labeled cells distinguishing desirable/undesirable traits; isolating genes in nuclear DNA according to a specified characteristic; isolating cells based on surface markers; isolating cells based on membrane integrity (viability), potential or predicted reproductive status (fertility), ability to survive freezing, etc.; isolating cells from contaminants or debris; isolating healthy cells from damaged cells (i.e., cancerous cells) (as in bone marrow extractions); red blood cells from white blood cells and platelets in a plasma mixture; and isolating any cells from any other cellular components, into corresponding fractions.

In addition, the subject matter of the present disclosure is also suitable for other medical applications as well. For example, the various laminar flows discussed below may be utilized as part of a kidney dialysis process, in which whole blood is cleansed of waste products and returned to the patient. Further, the various embodiments of the present disclosure may have further applicability to other biological or medical areas, such as for separations of cells, viruses, bacteria, cellular organelles or subparts, globular structures, colloidal suspensions, lipids and lipid globules, gels, immiscible particles, blastomeres, aggregations of cells, microorganisms, and other biological materials. For example, the component separation in accordance with the present disclosure may include cell "washing", in which contaminants (such as bacteria) are removed from cellular suspensions, which may be particularly useful in medical and food industry applications. Significantly, prior art flow-based techniques have not recognized any applicability to separation of non-motile cellular components, as have the present invention.

The subject matter of the present disclosure may also be utilized to move a species from one solution to another solution where separation by filtering or centrifugation is not practical or desirable. In addition to the applications discussed above, additional applications include isolating colloids of a given size from colloids of other sizes (for research or commercial applications), and washing particles such as cells, egg cells, etc. (effectively replacing the medium in which they are contained and removing contaminants), or washing particles such as nanotubes from a solution of salts and surfactants with a different salt concentration or without surfactants, for example.

The action of isolating species may rely on a number of physical properties of the objects or components including self-motility, self-diffusivity, free-fall velocity, or action under an external force, such as an actuator, an electromagnetic field or a holographic optical trap. The properties which may be sorted upon include, for example, cell motility, cell viability, object size, object mass, object density, the tendency of objects to attract or repel one another or other objects in the flow, object charge, object surface chemistry, and the tendency of certain other objects (i.e., molecules) to adhere to the object.

The various embodiments of the microfluidics chip, as described below, utilize one or more flow channels, having a plurality of substantially laminar flows, allowing one or more components to be interrogated for identification, and to be isolated into flows that exit into one or more outputs. In addition, the various components in the mixture may be isolated on-chip by using further isolation mechanisms, such as, for example, flow mechanisms, or optical tweezing or holographic optical trapping, or by magnetics (i.e., using magnetic beads). The various embodiments of the present invention thereby provide separation of components on a continuous basis, such as, within a continuous, closed system without the potential damage and contamination of prior art methods, particularly as provided in sperm separation. The continuous process of the present invention also provides significant time savings in isolating components.

While discussion below focuses on the separation of sperm into viable and motile sperm from non-viable or non-motile sperm, or isolating sperm by gender and other sex sorting variations, or isolating one or more labeled cells from un-labeled cells distinguishing desirable/undesirable traits, etc., the apparatus, methods and systems of the present invention may be extended to other types of particulate, biological or cellular matter, which are capable of being interrogated by fluorescence techniques within a fluid flow, or which are capable of being manipulated between different fluid flows into different outputs.

While the present subject matter is discussed in detail with respect to a microfluidic chip 100 illustrated in FIGS. 1-5 and a microfluidic chip holder 200 illustrated in FIGS. 6-9, it should be understood that this discussion applies equally to the various other embodiments discussed herein or any variation thereof.

Microfluidic Chip Assembly

FIG. 1 is an illustrative embodiment of a microfluidic chip 100. The microfluidic chip 100 is manufactured of a suitable thermoplastic (e.g., low auto-fluorescing polymer etc.) through an embossing process or injection molding process, as well known to one of ordinary skill in the art, and is of suitable size.

The microfluidic chip 100 includes a plurality of structural layers in which are disposed micro-channels which serve as sample input channel(s), sheath or buffer fluid channel(s), output channel(s), etc. The micro-channels are of suitable size to accommodate a particulate laminar flow, and may be disposed in any of the layers of the chip 100 in the appropriate length, as long as the object of the present invention is realized. The desired flow rate through the microfluidic chip 100 may be controlled by a predetermined introduction flow rate into the chip 100, maintaining the appropriate micro-channel dimensions within the chip 100, by pumping mechanisms, providing narrowing of the micro-channels at various locations, and/or by providing obstacles or dividers within the micro-channels.

A plurality of inputs is provided into the microfluidic chip 100, which provide access to the micro-channels/channels. In one embodiment, as shown in FIGS. 1-2, a sample input 106 is used for introducing a sample of components 160 in a sample fluid mixture 120 (see FIGS. 4-5) into a sample input channel 164A of the microfluidic chip 100 from a reservoir source (see FIG. 9). The microfluidic chip 100 also includes at least one sheath/buffer input (in one embodiment, sheath/buffer inputs 107, 108) for the introduction of sheath or buffer fluids. In one embodiment, there are two sheath/buffer inputs in the microfluidic chip 100, which include a sheath/buffer input 107 and sheath/buffer input 108, both disposed proximate to the sample input 106, and which both introduce sheath or buffer fluids into the microfluidic chip 100. The sheath or buffer fluids are well known in the art of microfluidics, and in one embodiment, may contain nutrients well known in the art to maintain the viability of the components 160 (i.e., sperm cells) in the fluid mixture. The location of the sheath/buffer inputs 107, 108 may vary, and they may access micro-channels in the chip 100 which are in the same or different structural layers.

In one embodiment, fill holes or air vents 121, 122—if not sealed—can be used to introduce sheath or buffer fluids into jet chambers 130, 131 (described later).

Figure 2A:
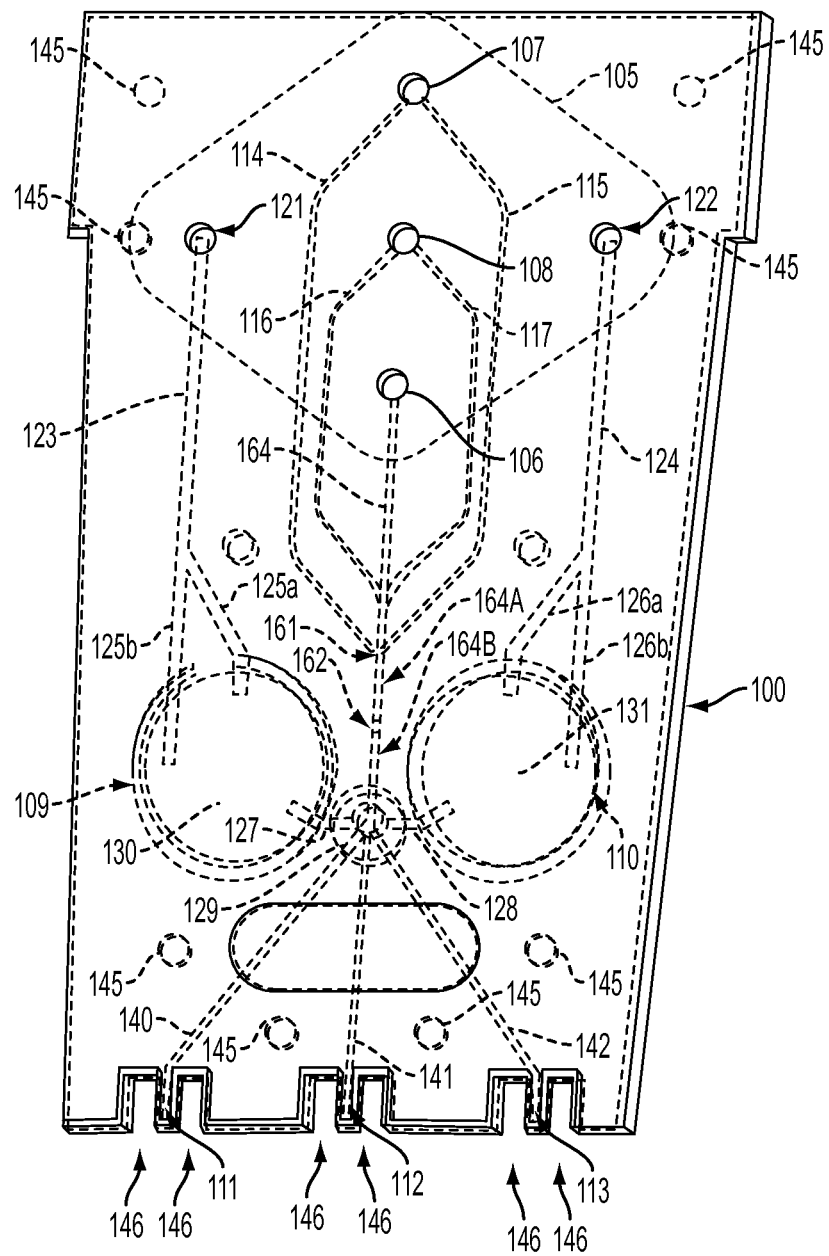
FIGS. 2A-2C show top views of the assembled microfluidic chip of FIG. 1, according to variant embodiments consistent with the present invention.

In one embodiment, a plurality of output channels stemming from main channel 164 (see FIG. 2A) is provided for removal of fluid which has flowed through the microfluidic chip 100, including the isolated components 160 and/or sheath or buffer fluids. In one embodiment as shown in FIGS. 1-2, there are three output channels 140-142 which include a left side output channel 140, a center output channel 141, and a right side output channel 142. The left side output channel 140 ends at a first output 111, the center output channel 141 ends at a second output 112 and the right side output channel 142 ends at a third output 113. However, the number of outputs may be less or more depending on the number of components 160 to be isolated from the fluid mixture 120.

In one embodiment, instead of a straight edge, where necessary, a plurality of notches or recesses 146 are disposed at a bottom edge of the microfluidic chip 100 to separate the outputs (i.e., outputs 111-113) and for attachment of external tubing etc. The first output 111, the second output 112 and the third output 113 are reached via output channels 140-142 which originate from interrogation chamber 129 (see FIGS. 2A-4).

In one embodiment, the microfluidic chip 100 has a plurality of structural layers in which the micro-channels are disposed. The channels may be disposed in one or more layers or in-between layers. In one embodiment, as shown in FIG. 1, as an example, four structural plastic layers 101-104 are shown to comprise the microfluidic chip 100. However, one of ordinary skill in the art would know that less or additional layers may be used, and the channels may be disposed in any of the layers as long as the object of the present invention is achieved.

Figure 6:
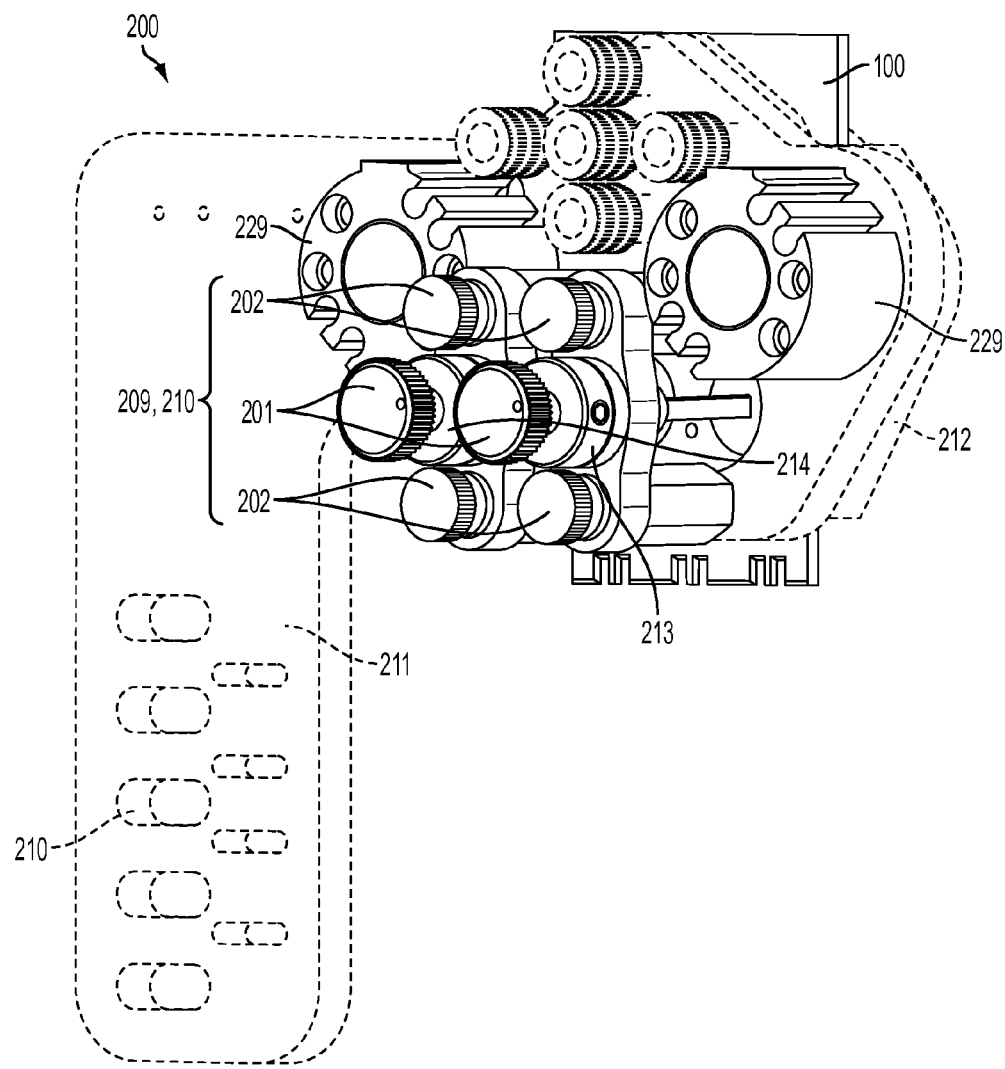
FIG. 6 shows a schematic illustration of a front view of a main body of a microfluidic chip holder, according to one embodiment consistent with the present invention.
Figure 7:
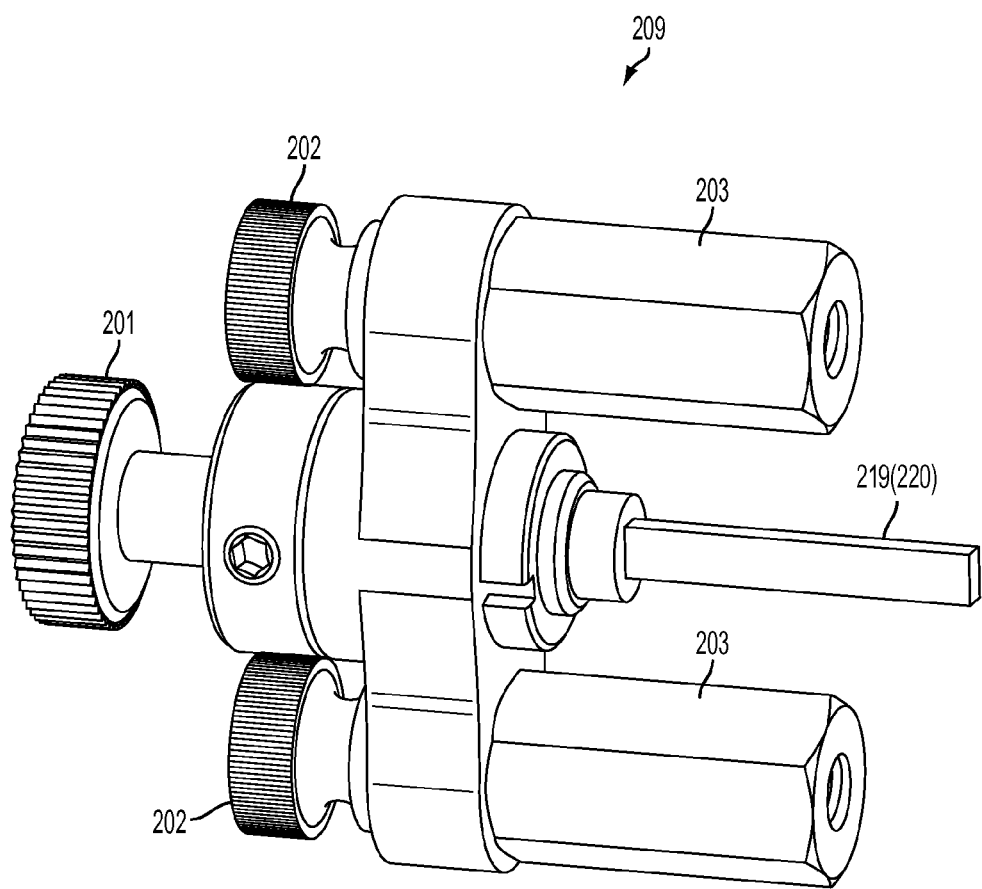
FIG. 7 shows a schematic illustration of a side view of a piezoelectric actuator assembly of the microfluidic chip holder of FIG. 6, according to one embodiment consistent with the present invention.
Figure 8:
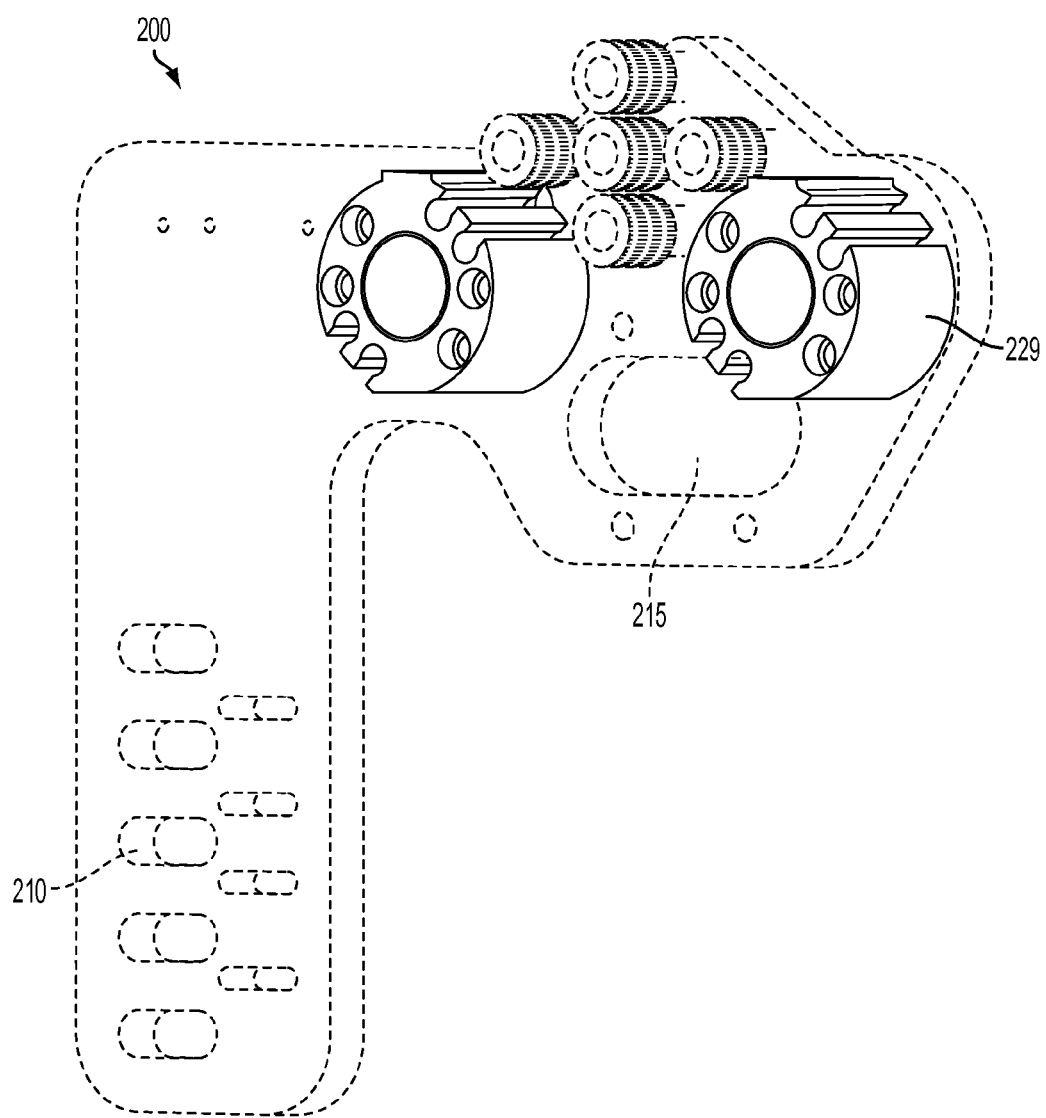
FIG. 8 shows a schematic illustration of a front view of a microfluidic chip holder, according to one embodiment consistent with the present invention.

A gasket of any desired shape, or O-rings, may be provided to maintain a tight seal between the microfluidic chip 100 and the microfluidic chip holder 200 (see FIG. 6). In the case of a gasket, it may be a single sheet or a plurality of components, in any configuration, or material (i.e., rubber, silicone, etc.) as desired. In one embodiment, as shown in FIG. 1, a first gasket 105 is disposed at one end of the microfluidic chip 100 and interfaces, or is bonded (using an epoxy) with layer 104. A plurality of holes 144 are provided in the first gasket 105 and are configured to align with the sample input 106, sheath/buffer input 107, sheath/buffer input 108, and air vents 121, 122, to provide access thereto.

In one embodiment, a second gasket 143 is disposed at another end of the microfluidic chip 100 opposite to the first gasket 105, and interfaces or is bonded with (using epoxy) the top structural layer 104. The second gasket 143 is configured to assist sealing, as well as stabilizing or balancing the microfluidic chip 100 in the microfluidic chip holder 200 (see FIG. 6).

In one embodiment, holes and posts 145 are disposed at various convenient positions in the microfluidic chip 100 to fix and align the multiple layers (i.e., layers 101-104) during chip fabrication.

Figure 4:
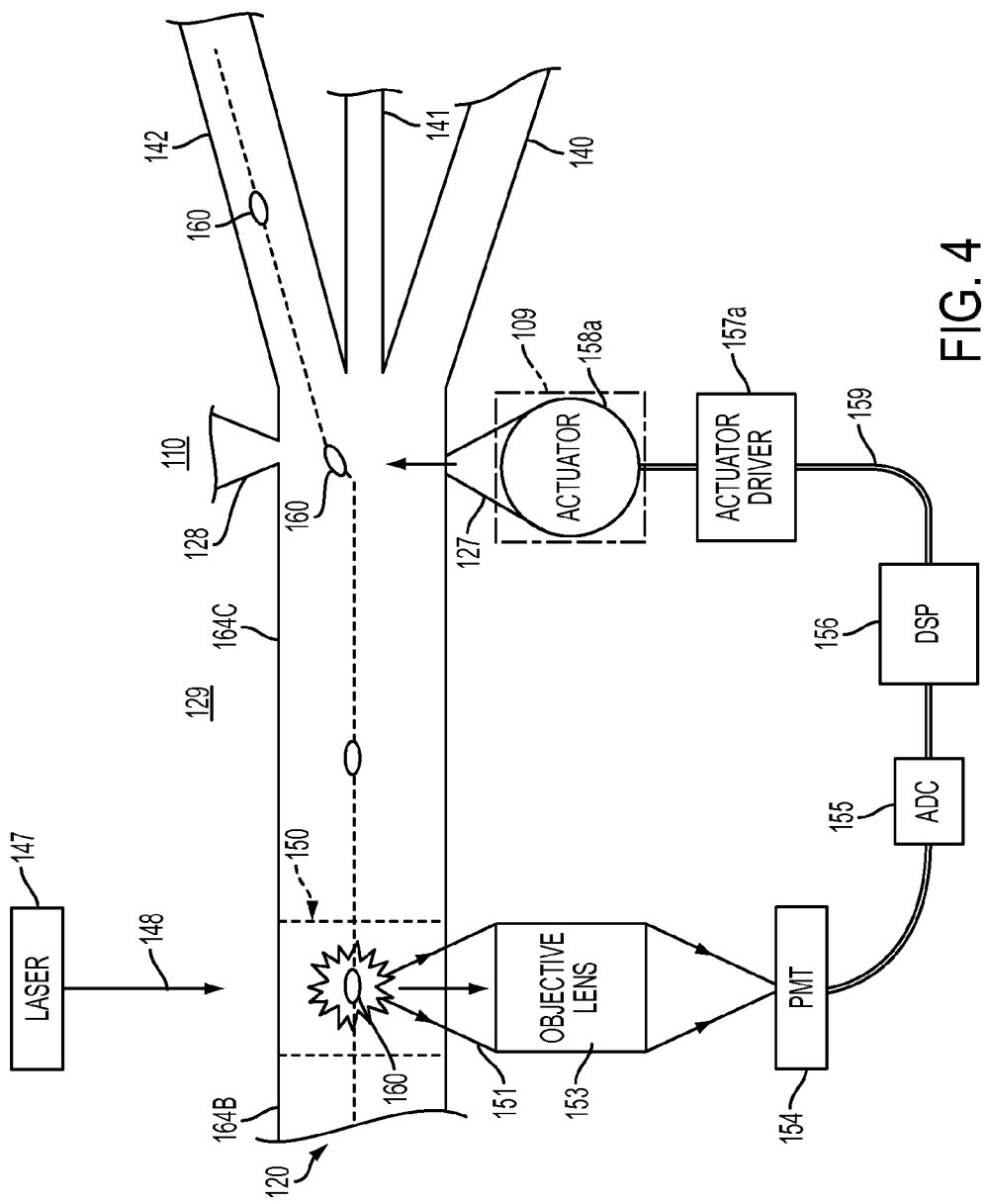
FIG. 4 shows a cross-sectional internal view of an illustrative interrogation by a light source of components flowing in a fluid mixture, through the microfluidic chip of FIGS. 1-2, and an illustrative action of one of two (mirrored) piezoelectric actuator assemblies, according to one embodiment consistent with the present invention.

In one embodiment, a sample fluid mixture 120 including components 160 is introduced into sample input 106, and the fluid mixture 120 flows through main channel 164 toward interrogation chamber 129 (see FIGS. 2A, 4, and 5). The sheath or buffer fluids 163 are introduced into sheath/buffer inputs 107, 108, and flow through channels 114, 115 and 116, 117, respectively, into the main channel 164, and towards the interrogation chamber 129 before flowing out through output channels 140-142.

In one embodiment, sheath or buffer fluids 163 can be introduced into jet chambers 130, 131 through air vents 121, 122 to fill the chambers 130, 131 after manufacture of the microfluidic chip 110, if the chambers 130, 131 are not filled with sheath or buffer fluids 163 during manufacture. As stated above, the sheath or buffer fluids 163 used are well known to one of ordinary skill in the art of microfluidics.

In one embodiment, the fluid mixture 120 from main channel 164 joins with the sheath or buffer fluids 163 from channels 114, 115 at intersection 161 in the same plane of the microfluidic chip 100. In one embodiment, buffer fluids 163 from channels 116, 117 join the combined fluid mixture 120 and sheath or buffer fluids 163 from first intersection 161, downstream at second intersection 162. In one embodiment, channels 114, 115 are substantially the same dimensions as channels 116, 117, as long as the desired flow rate(s) is achieved to accomplish the object of the present invention.

In one embodiment, channels 114-117, 123, 124, 140-142, 125a, 125b, 126a, 126b, 127, 128 may have substantially the same dimensions, however, one of ordinary skill in the art would know that the size of any or all of the channels in the microfluidic chip 100 may vary in dimension (i.e., between 50 and 500 microns), as long as the desired flow rate(s) is achieved to accomplish the object of the present invention.

In one embodiment, the channels 114-117, 123, 124, 140-142, 125a, 125b, 126a, 126b, 127, 128, of the microfluidic chip 100, may not just vary in dimension, but may have tapered shapes at entry points to other channels in the chip 100 in order to control the flow of fluid through the channels. For example, main channel 164 may taper at the entry point into intersection 161 (see FIG. 5B), to control and speed up the flow of sample 120 into the intersection 161, and allow the sheath or buffer fluids 163 from channels 114, 115 to compress the sample 120 fluid mixture in a first direction (i.e., horizontally), on at least two sides, if not all sides (depending on where the tapered channel 164 joins channel 164A). Thus, the sample fluid mixture 120 becomes a relatively smaller, narrower stream, bounded or surrounded by sheath or buffer fluids 163, while maintaining laminar flow in channel 164A. However, one of ordinary skill in the art would know that the main channel 164 entering into intersection 161 could be of any physical arrangement, such as a rectangular or circular-shaped channel, as long as the object of the present invention is obtained.

In one exemplary embodiment, at least one of the channels 116, 117 is disposed in a different structural layer of the microfluidic chip 100, than the layer in which the channel 164 is disposed. For example, channel 116 may be disposed in layer 103 and channel 117 may be disposed in layer 101 (see FIG. 1), such that channels 116, 117 are at different planes from the other channels 164 and 114, 115 (in layer 102), when the sheath or buffer fluids 163 join the fluid mixture 120 at intersection 162. In one embodiment, main channel 164 is disposed between layers 102, 103 (see FIG. 3); however, one of ordinary skill in the art would know that the channels 114-117, 164, 123, 124, 140-142, 125a, 125b, 126a, 126b, 127, 128 etc., can be disposed in any layer or between any two layers. Further, although the channels 114-117, 164, 123, 124, 140-142, 125a, 125b, 126a, 126b, 127, 128 etc. are described in exemplary embodiments as shown in the Figures, one of ordinary skill in the art would know that the particular arrangement or layout of the channels on the chip 100 may be in any desired arrangement as long as they achieve the described features of the present invention.

In one embodiment, the sheath or buffer fluids in channels 116, 117 join the fluid mixture via holes cut in the layers 101-103 at substantially vertical positions above and below the intersection 162. The sheath or buffer fluids from channels 116, 117 compress the fluid mixture 120 flow in a perpendicular manner with respect to channel 164B, such that the components 160 in the fluid mixture 120 are compressed or flattened, and oriented in the selected or desired direction (see below), while still maintaining laminar flow in channel 164B.

In one embodiment, as shown in FIGS. 1-2, channels 114, 115 and 116, 117 are depicted as partially coaxial to one another with a center point defined by the sample input 106. Thus, in one embodiment, channels 114, 115 and 116, 117 are disposed in a substantially parallel arrangement, with the channels 114, 115 and 116, 117 being equidistant to main channel 164. However, one of ordinary skill in the art would recognize that the depicted configuration may be different as long as it achieves the desired features of the present invention.

Further, in one embodiment, channels 114, 115 preferably join intersection 161 in the same plane, at an angle of 45 degrees or less, whereas channels 116, 117, which parallel sample input channel 164A, join intersection 162 from different layers, at an angle of substantially 90 degrees. However, one of ordinary skill in the art would appreciate that the depicted configurations, angles, and structural arrangements of the microfluidic chip 100 layers and channels may be different as long as they achieve the desired features of the present invention.

In one embodiment, downstream from intersection 162, the components 160 in the fluid mixture 120 flow through channel 164B into an interrogation chamber 129, where the components 160 are interrogated.

In one embodiment, a flexible diaphragm 170, 171 (see FIG. 1) made from a suitable material, such as one of stainless steel, brass, titanium, nickel alloy, polymer, or other suitable material with desired elastic response, covers jet chambers 130, 131. In one embodiment, an actuator is disposed on at least one side of channel 164B and the interrogation chamber 129 (see FIGS. 2A and 2B), in order to cause mechanical displacement of the diaphragm 170, 171, in order to jet or push sheath or buffer fluids 163 from one of the jet chambers 130, 131 on that side of channel 146B, to push components 160 from channel 164C into one of the output channels 140, 142 on the other side of the channel 164B. In other words, the actuator would jet sheath or buffer fluids 163 from jet chamber 130 into channel 164C, and push target components 160 in channel 164C into output channel 142 to isolate the target components from the fluid mixture 120. This embodiment is useful when only one type of target components 160 are isolated (which may require only two output channels 141, 142, for example, instead of three output channels 140-142) (see FIG. 2B).

The actuator may be one of a piezoelectric, magnetic, electrostatic, hydraulic, or pneumatic type actuator. Although a disc-shaped actuator assembly (i.e., 109, 110) is shown in FIGS. 1-2, one of ordinary skill in the art would know that any type or shape of actuator which performs the needed function could be used.

Figure 2B:
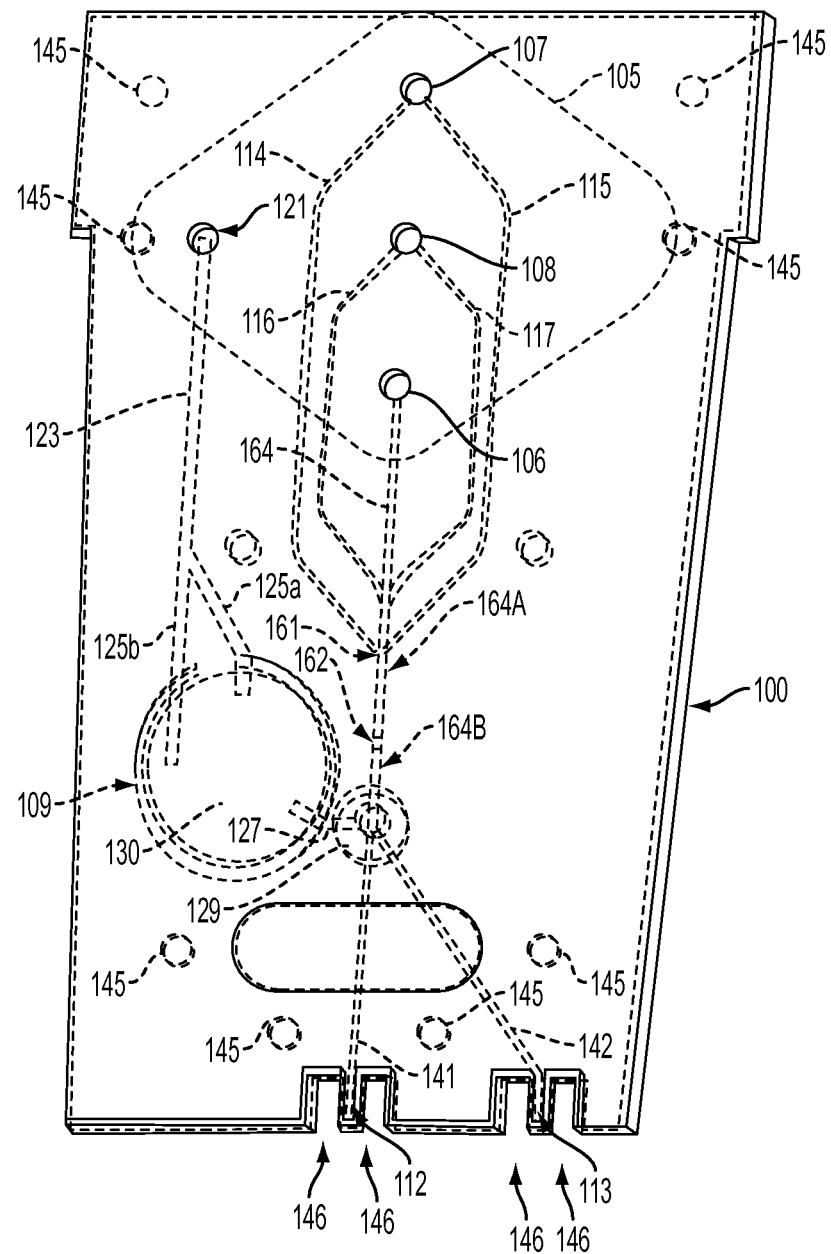
Figure 2C:
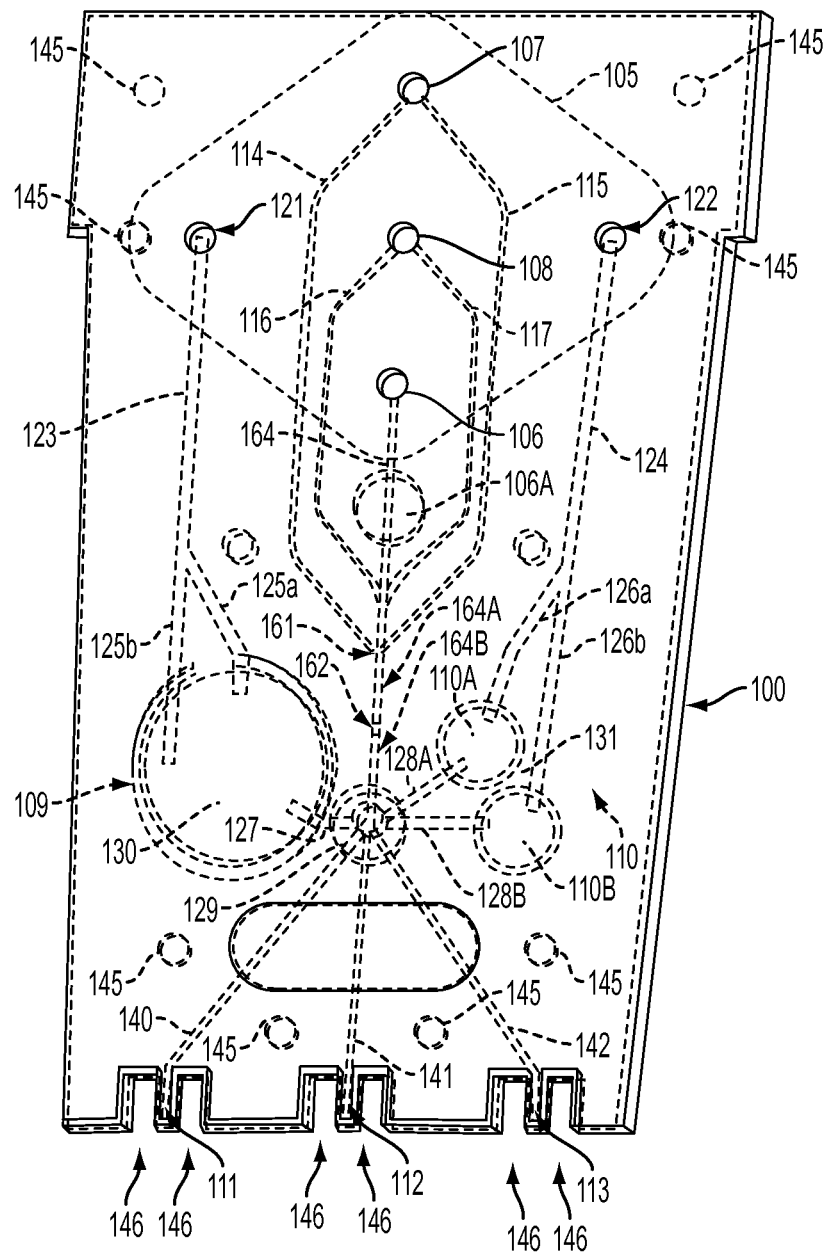

In other embodiments, the actuator is disposed on either side of channel 164B (as shown in FIG. 2A), but in other embodiments, more than one actuator (of a relatively smaller size) may be disposed on one or more sides of channel 164B and connected to channel 164B via jet channels (see FIG. 2C).

The following description of the function of the actuator(s) will be made with reference to FIG. 2A, although one of ordinary skill in the art would know that any type of actuator disposed in a location on the chip 100 would be acceptable, as long as it achieved the features of the present invention.

In one embodiment, in order to activate the diaphragms 170, 171 and jet the sheath or buffer fluids 163 from chambers 130, 131 into channel 164B, two external, stacked piezoelectric actuator assemblies 209, 210 are provided (see FIGS. 6 and 7) which align with and actuate the diaphragms 170, 171. The external, stacked piezoelectric actuator assemblies 209, 210 are disposed in a microfluidic chip holder 200. The stacked piezoelectric actuator assemblies 209, 210 each include a piezoelectric actuator 219, 220, respectively, which have a high resonant frequency, and which each are disposed at a position in a center of, and in contact with the diaphragm 170, 171, to squeeze the sheath or buffer fluids 163 from the chamber 130, 131 into channel 164C.

The microfluidic chip holder 200 may be of any type known to one of ordinary skill in the art, and is configured to precisely position piezoelectric actuators 219, 220, such that the piezoelectric actuators 219, 220 may maintain constant contact with diaphragms 170, 171 of the microfluidic chip 100. For example, in one embodiment, this is accomplished by each piezoelectric actuator assembly 209, 210 being mounted (or adhered using a suitable epoxy) on lockable adjustment screws 201 which move the piezoelectric actuators 219, 220 into position against the diaphragms 170, 171, respectively; and thumb screws 202 with threaded bodies that act to move the screws 202 against the diaphragms 170, 171 for stabilization. A spacer 203 attached to the piezoelectric actuator 219, 220 allows a feasible contact to be made between it and a diaphragm 170, 171 of the microfluidic chip 100. The adjustment screws 201 allow a user to adjust the position of the piezoelectric actuators 209, 210 relative to the microfluidic chip 100 for both coarse and fine adjustment. The thumb screws 202 may be tightened to secure the piezoelectric assemblies 209, 210 to the main chip body 100 or loosened to remove the piezoelectric actuator assemblies 209, 210 from the main chip body 100.

In one embodiment, at least one piezoelectric actuator (209 or 210) is mounted on a plate (not shown) which can be translated in direction normal to the diaphragm (170 or 171) of the microfluidic chip 100. An adjustment screw 201 is mounted on the holder 200 and can be extended and retracted by turning the screw 201. The tip of the adjustment screw 201 is against the plate. As the screw 201 is extended, the plate along with the piezoelectric actuator 209, 210, is pushed toward the diaphragm 170, 171 in a translation motion, such that a feasible contact is made between the piezoelectric actuator 209, 210 and the diaphragm 170, 171. With this method, the positioning of the piezoelectric actuators 209, 210 is adjusted through translation of the piezoelectric actuators 209, 210 only, while in the previous embodiment where the piezoelectric actuator 209, 210 is mounted directly on the adjustment screw 201, the positioning of the piezoelectric actuator 209, 210 is a combination of translation and rotation of the piezoelectric actuator 209, 210, during which damage can be caused on the delicate piezoelectric actuator 209, 210.

In another embodiment, an electronic circuit is connected to the stacked piezoelectric actuator assembly 209, 210 before driving it. When each of the stacked piezoelectric actuators 219, 220 is in contact with the respective diaphragm 170, 171, the resistance force from the diaphragm 170, 171 causes the strain on the stacked piezoelectric actuator 219, 220, which generates an electronic signal. Thus, the electronic circuit is able to amplify the electronic signal to a predetermined value to trigger an LED (light emitting diode). When the stacked piezoelectric actuator 219, 220 is in contact with the diaphragm 170, 171 the LED is turned on automatically, which indicates contact between the stacked piezoelectric actuator 219, 220 and the diaphragm 170, 171 is made. This contact sensing allows enough force for the actuators 219, 220 to compress the chambers 130, 131 to jet fluid 163 into the channel 164B.

It would be clear to one of ordinary skill in the art that the LED is one example of an indicator of contact. For example, once contact is made, and the electronic signal exceeds a set threshold, a feedback is generated for the user, which can be in any of the following forms: a light (i.e., LED), a sound (i.e., buzzer), a haptic (i.e., vibrator), or any combination thereof. Thus, the user can stop adjusting the contact and sustain the contact. Of course, in one embodiment, the above-described procedure may be automated.

In an alternative embodiment, instead of at least one external stacked piezoelectric actuator assembly, a thin film of piezoelectric material (well-known to one of ordinary skill in the art) is directly deposited on the top surface of at least one diaphragms 170, 171, to form at least one piezoelectric actuator assembly 109, 110 (see FIGS. 2A and 4) to displace (bend) the respective diaphragm 170, 171 and drive the fluids in the respective jet chamber 130, 131 into channel 164C, respectively. The piezoelectric material is permanently bonded with the previously described flexible diaphragm 170, 171 by an adhering mechanism. Thus, in this embodiment, when voltage is applied across the electrodes of the piezoelectric actuator assembly 109, 110, the whole diaphragm 170, 171 bends into the chamber 130, 131 and squeezes the fluid 163 therein, into the channel 164C to deflect the target or selected components 160 into a side output channel 140, 142.

As stated above, with respect to either the external stacked piezoelectric actuator assemblies 209, 210 or piezoelectric actuator assemblies 109, 110, in one embodiment, only one piezoelectric actuator assembly may be required to jet sheath or buffer fluids 163 from jet chamber 130 into channel 164C, and push target components 160 in channel 164C into output channel 142 to isolate the target components from the fluid mixture 120, as shown in FIG. 2B.

In one embodiment, the piezoelectric actuator assemblies 109, 110 are used to seal the jet chambers 130, 131, respectively, at layer 103, for example—but one of ordinary skill in the art would know that it could be in any structural layer—after the chambers 130, 131 are filled with sheath or buffer fluids 163, to make the microfluidic chip 100 impervious to fluid leakage.

Thus, the piezoelectric actuator assemblies 109, 110 satisfy the requirement of low flow rates considering the relatively small bend displacement of the diaphragms 170, 171, and low force thereon, in contrast to the large displacement and strong force applied by the external, stacked piezoelectric actuator assemblies 209, 210 which are able to work at very high flow rates. However, one of ordinary skill in the art would know that the actuator assemblies 109, 110, 209, 210 can be chosen independently for use in the microfluidic chip 100 based upon the different operation speeds and flow rate requirements.

In one embodiment, a thin piezoelectric film disposed on top of the diaphragm 170, 171 works as a strain sensor to determine how much strain or displacement the external, stacked piezoelectric actuator assemblies 209, 210 generate as they are triggered by the electronic signal to displace the respective diaphragms 170, 171. The diameter and thickness of the piezoelectric thin film depends on the cross-section of the external, stacked piezoelectric actuator 219, 220 and the force generated on the diaphragm 170, 171. The piezoelectric thin film and diaphragm 170, 171 may be different from the one discussed above in the alternative embodiment.

The filling of the jet chambers 130, 131 is now described. In one embodiment, air vents 121, 122 are provided to remove air from jet chambers 130, 131 respectively (see FIG. 2A), after manufacturing when the chambers 130, 131 are filled with sheath or buffer fluids 163—forcing air out through the air vents 121, 122—and before the chambers 130, 131 are sealed with sheath or buffer fluids 163 therein. Alternatively, in another embodiment, if the air vents 121, 122 are left open, then sheath or buffer fluids 163 may be introduced through the vents 121, 122 into the chambers 130, 131 if this is not done during manufacturing. The sheath of buffer, or other fluids 163 disposed in the jet chambers 130, 131 may be the same or different from the sheath or buffer fluids 163 inputted through channels 114, 115, 116, or 117.

In one embodiment, if sheath or buffer fluids 163 are used to fill up the jet chambers 130, 131, they may be inputted through inputs 121, 122 and flowed through channels 123, 124 respectively, to enter jet chamber 130 via channels 125a and 125b, and jet chamber 131 via channels 126a and 126b.

In one embodiment, jet channel 127 leaves jet chamber 130, and jet channel 128 leaves jet chamber 131, and both jet channels 127, 128 enter the interrogation chamber 129 (see FIG. 2A). The jet channels 127, 128 may be disposed in any layer of the chip 100 and enter the channel 164C at any angle in the same plane.

In one embodiment, in order to form a strong, instantaneous jet stream, the jet channels 127, 128 may be tapered when they connect to the main channel 164C. However, one of ordinary skill in the art would know that the jet channels 127, 128 may have a particular angle, or be of a different structure, as long as they achieve the described features of the present invention.

In one embodiment, the jet channels 127, 128 work to displace or bend the diaphragms 170, 171, respectively, and jet or squeeze sheath or buffer fluids 163 into the channel 164C. However, when the diaphragms 170, 171 return to a neutral (unbent) position, the jet channels 127, 128 which issue from jet chambers 130, 131, work as diffusers to ensure that a net fluid volume from the jet chambers 130, 131 to the channel 164C is maintained, and that it is easy to refill the chambers 130, 131 with sheath or buffer fluids 163.

In one embodiment, output channels 140-142 depart from channel 164C within interrogation chamber 129 to outputs 111-113. As stated above, in one embodiment, more than one on-chip piezoelectric actuator assembly 109, 110, or external, stacked piezoelectric actuator assembly 209, 210 (in any size or location) may be used to connect to each of jet channels 127, 128, to provide additional power to jet sheath or buffer fluids 163 from jet chambers 130, 131 into channel 164C. In one embodiment, the distance from each of the jet channels 127, 128 entries into channel 164C to each of the output channels 140-142 should be shorter than the distance between components 160, to avoid target components 160 mixing with undesired components 160 (further described below). In one embodiment, the cross-section and the length of the output channels 140-142 should be maintained at a predetermined volume ratio (i.e., 2:1:2, or 1:2:1 etc.) to obtain the desired hydraulic resistance of the output channels 140-142.

In one embodiment, an interrogation apparatus is disposed downstream from where channels 116, 117 enter into channel 164B. In one embodiment, channel 164B tapers into the interrogation chamber 129, which speeds up the flow of the fluid mixture through the interrogation chamber 129. However, one of ordinary skill in the art would know that the channel 164B need not taper and could be of any dimension and size as long as the present invention performs according to the desired requirements.

An interrogation apparatus is used to interrogate and identify the components 160 in the fluid mixture in channel 164B passing through the interrogation chamber 129. Note that channel 164B may be disposed in a single layer (i.e., layer 102) or disposed in between layers (i.e., layers 102, 103). In one embodiment, the interrogation chamber 129 includes an opening or window 149 (see FIG. 3) cut into the microfluidic chip 100 in at least the uppermost layer (i.e., layer 104 or other), and another opening or window 152 is cut into the chip 110 in at least the lowermost layer (i.e., layer 101 or other).

Figure 3:
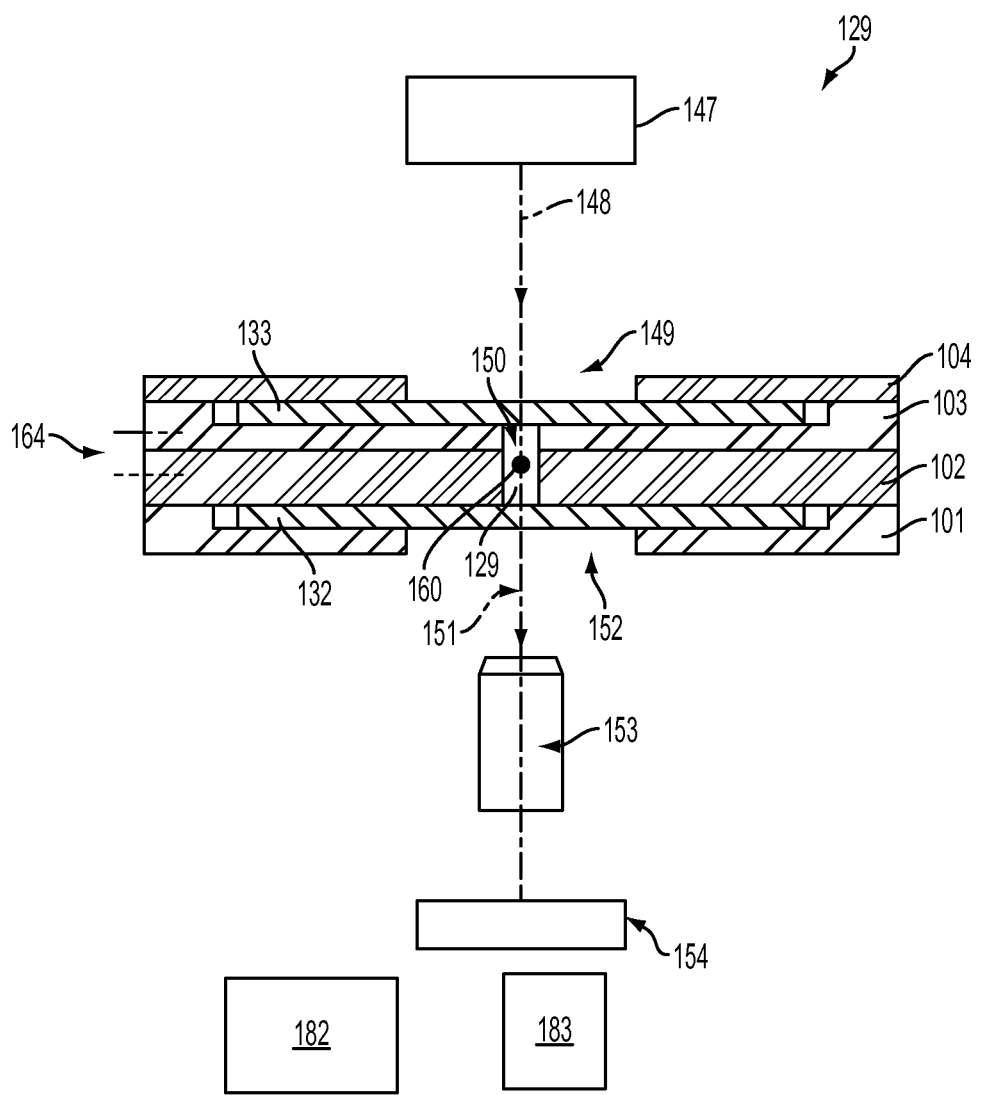
FIG. 3 shows a cross-sectional view of an interrogation chamber of the microfluidic chip of FIGS. 1-2, according to one embodiment consistent with the present invention.

In one embodiment, an opening 150 is cut into the microfluidic chip through layers 101-104. In one embodiment, the top window 149 is configured to receive a first covering 133 and the bottom window 152 is configured to receive a second covering 132. However, the windows 149, 152 may be located in any suitable layer and need not be in the uppermost/lowermost layers. The coverings 133, 132 may be made of any material with the desired transmission requirements, such as plastic, glass, or may even be a lens. Note that although the relative diameters of the windows 149, 152 and opening 150 are shown in FIG. 3, these may vary according to manufacturing considerations.

In one embodiment, the above-mentioned first and second coverings 133, 132 are configured to enclose the interrogation chamber 129. The windows 149, 152 and coverings 133, 132 (see FIG. 3), allow the components 160 flowing in the fluid mixture 120 in channel 164B (see FIG. 5A) through the interrogation chamber 129, to be viewed through opening 150, and acted upon by a suitable light source 147 configured to emit a high intensity beam 148 with any wavelength that matches excitable components in the fluid mixture 120. Although a laser 147 is shown, any suitable other light sources may be used, such as a light emitting diode (LED), arc lamp, etc. to emit a beam which excites the components.

In one embodiment, a high intensity laser beam 148 from a suitable laser 147 of a preselected wavelength—such as a 355 nm continuous wave (CW) (or quasi-CW) laser 147—is required to excite the components 160 in the fluid mixture (i.e., sperm cells). In one embodiment, the laser 147 (see FIG. 3) emits a laser beam 148 through window 149 in layer 104, through the covering 133 at an uppermost portion of the chip 100, through opening 150, and through covering 132 and window 152 in layer 101 of the chip 100, to illuminate the components 160 flowing through channel 164B in interrogation region 129 of the chip 100.

In one embodiment, the light beam 148 can be delivered to the components 160 by an optical fiber that is embedded in the microfluidic chip 100 at opening 150.

The high intensity beam 148 interacts with the components 160 (see detailed explanation below), and passes through the first and second coverings 133, 132, to exit from bottom window 152, such that the emitted light 151, which is induced by the beam 148, is received by an objective lens 153. The objective lens 153 may be disposed in any suitable position with respect to the microfluidic chip 100. Because the interrogation chamber 129 is sealed by the first and second coverings 133, 132, the high intensity beam 148 does not impinge on the microfluidic chip 100 and damage the layers 101-104. Thus, the first and second coverings 133, 132 help prevent damage to the microfluidic chip 100 from the high intensity beam 148 and photonic noise induced from the microfluidic chip material (i.e., plastic).

In one embodiment, the emitted light 151 received by the objective lens 153 is converted into an electronic signal by an optical sensor 154, such as a photomultiplier tube (PMT) or photodiode, etc. The electronic signal can be digitized by an analog-to-digital converter (ADC) 155 and sent to a digital signal processor (DSP) based controller 156. The DSP based controller 156 monitors the electronic signal and may then trigger one of two actuator drivers (i.e., 157a, 157b) at a predetermined value, to drive a relevant one of the two piezoelectric actuator assemblies (109, 110, or 209, 210). In one embodiment (shown in FIG. 2A), the piezoelectric drivers and piezoelectric actuators (158a, 158b, or 219, 220) are part of two piezoelectric actuator assemblies (109, 110, or 209, 210) respectively, disposed on either side of the interrogation chamber 129. The trigger signal sent to the piezoelectric actuators (109, 110, or 219, 220) is determined by the sensor raw signal, to activate the particular piezoelectric actuator assembly (109, 110, 209, 210) when the selected component is detected.

In the embodiment with the bonded piezoelectric actuator assemblies 109, 110, the thickness of the diaphragm 170, 171 may be different and is dependent upon the voltage applied via electrical wires through the actuator assembly 109, 110 on the chip 100. When the electronic signal is sent through an electronic circuit directly to the actuator assemblies (i.e., 109, 110), the diaphragms 170, 171 bend and change (increase) the pressure in the chambers 130, 131.

The at least one of the piezoelectric actuator assemblies (109, 110, or 209, 210) is used to act upon the desired components 160 in the fluid mixture in channel 164C, as the components 160 leave the opening 150 for interrogation area 129 after interrogation. Although actuator driver 157b and piezoelectric actuator assembly 110 are not illustrated in FIG. 4, the operation and configuration of actuator driver 157b and piezoelectric actuator assembly 110 are the same as that of the actuator driver 157a and the piezoelectric actuator assembly 109. Thus, piezoelectric actuator 157b acts to deflect components 160 in the flow stream in channel 164C to the right output channel 142, and to the third output 113. The same operation applies for the piezoelectric actuator assembly 110, which jets sheath or buffer fluid 163 from the jet chamber 131 via jet channel 128, and deflects target or selected components 160 to the left output channel 140 and the third output 113.

In an alternative embodiment, a piezoelectric actuator assembly 106A (i.e., a piezoelectric disc similar to the piezoelectric actuator assemblies 109, 110, and of a suitable size— see FIG. 2C), or a suitable pumping system (see FIG. 9, for example—discussed later), is used to pump sample fluid 120 in channel 164 toward intersection 161. The sample piezoelectric actuator assembly 106A would be disposed at sample input 106. By pumping the sample fluid mixture 120 into the main channel 164, a measure of control can be made over the spacing of the components 160 therein, such that a more controlled relationship may be made between the components 160 as they enter the main channel 164.

If the piezoelectric actuator assemblies 109, 110 are not employed, the (target) components 160 proceed from main channel 164 to the center output channel 141, and to the second output 112, and the sheath or buffer fluids 163 proceed through output channels 140, 142, to outputs 110, 112, respectively.

In one embodiment, the output channels 140-142 increase in dimension from the channel 164C, leaving the interrogation chamber 129, such that the output ratio for enrichment of the isolated component 160, is increased through the relevant channel(s).

Chip Operation

In one embodiment, the microfluidic chip 100 is provided in a sterile state, and may be primed with one or more solutions (i.e., sheath or buffer fluids 163), or purged of any fluids or materials by either draining the microfluidic chip 100 or by flowing sheath or buffer fluids 153 or other solutions through the microfluidic chip 100, according to known methods. Once the microfluidic chip 100 is primed, and the jet chambers 130, 131 are filled with sheath or buffer fluids 163, either during manufacturing, or thereafter (as described above), the air vents 121, 122 are sealed. As stated above, in another embodiment, the air vents 121, 122 may be left open for additional sheath or buffer fluids 163 to be added to the chambers 130, 131 during operation.

In one embodiment, as stated above, the components 160 that are to be isolated include, for example: isolating viable and motile sperm from non-viable or non-motile sperm; isolating sperm by gender, and other sex sorting variations; isolating stems cells from cells in a population; isolating one or more labeled cells from un-labeled cells distinguishing desirable/undesirable traits; sperm cells with different desirable characteristics; isolating genes in nuclear DNA according to a specified characteristic; isolating cells based on surface markers; isolating cells based on membrane integrity (viability), potential or predicted reproductive status (fertility), ability to survive freezing, etc.; isolating cells from contaminants or debris; isolating healthy cells from damaged cells (i.e., cancerous cells) (as in bone marrow extractions); red blood cells from white blood cells and platelets in a plasma mixture; and isolating any cells from any other cellular components, into corresponding fractions; damaged cells, or contaminants or debris, or any other biological materials that are desired to isolated. The components 160 may be cells or beads treated or coated with, linker molecules, or embedded with a fluorescent or luminescent label molecule(s). The components 160 may have a variety of physical or chemical attributes, such as size, shape, materials, texture, etc.

In one embodiment, a heterogeneous population of components 160 may be measured simultaneously, with each component 160 being examined for different quantities or regimes in similar quantities (e.g., multiplexed measurements), or the components 160 may be examined and distinguished based on a label (e.g., fluorescent), image (due to size, shape, different absorption, scattering, fluorescence, luminescence characteristics, fluorescence or luminescence emission profiles, fluorescent or luminescent decay lifetime), and/or particle position etc.

Figure 5A:
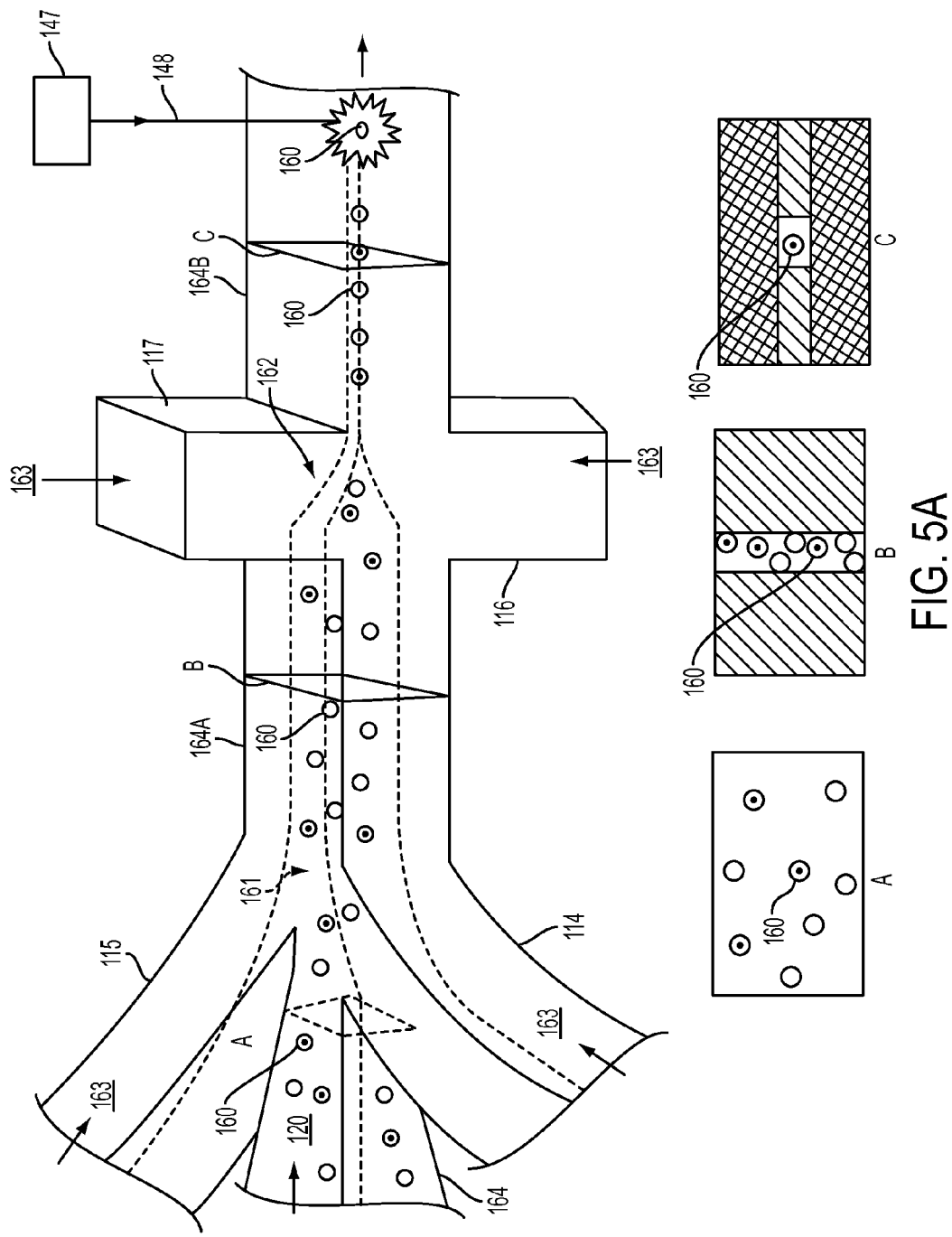
FIG. 5A shows a perspective internal, and oblique view of components flowing through the microfluidic chip of FIGS. 1-2, and an illustrative operation of two-step focusing, according to one embodiment consistent with the present invention.
Figure 5B:
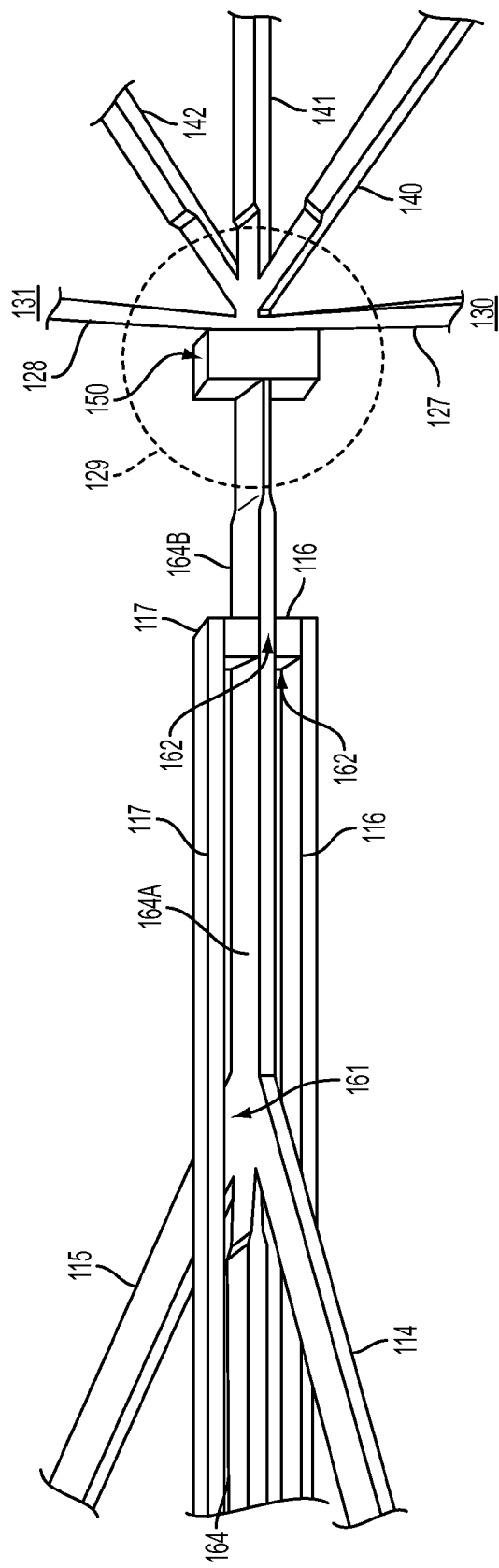
FIG. 5B shows a perspective oblique view of the channels and interrogation chamber disposed in the microfluidic chip of FIGS. 1-2C, according to one embodiment consistent with the present invention.

In one embodiment, a two-step focusing method of a component sorting system consistent with the present invention may be used, as illustrated in FIG. 5A, in order to position the components 160 in channel 164B for interrogation in the interrogation chamber 129.

In one embodiment, the first focusing step of the present invention is accomplished by inputting a fluid sample 120 containing components 160, such as sperm cells etc., through sample input 106, and inputting sheath or buffer fluids 163 through sheath or buffer inputs 107, 108. In one embodiment, the components 160 are pre-stained with dye (e.g., Hoechst dye), in order to allow fluorescence, and for imaging to be detected. In one embodiment, sheath or buffer fluids 163 are disposed in jet chambers 130, 131, and inputs 121, 122 sealed.

In one embodiment, as shown in FIG. 5A, components 160 in the sample fluid mixture 120 flow through main channel 164, and have random orientation and position (see inset A). At intersection 161, the sample mixture 120 flowing in main channel 164 is compressed by the sheath or buffer fluids 163 from channels 114, 115, in a first direction (i.e., at least horizontally, on at least both sides of the flow, if not all sides depending on where the main channel 164 enters the intersection 161), when the sheath or buffer fluids 163 meet with the sample mixture 120. As a result, the components 160 are focused around the center of the channel 164, and may be compressed into a thin strip across the depth of the channel 164A. The intersection 161 leading into channel 164A is the focusing region. Thus, at intersection 161, as the sample 120 is being compressed by the sheath or buffer fluids 163 from channels 114, 115, toward the center of the channel 164A, the components 160 (i.e., sperm cells) move toward the center of the channel 164 width.

In one embodiment, the present invention includes a second focusing step, where the sample mixture 120 containing components 160, is further compressed by sheath or buffer fluids 163 from a second direction (i.e., the vertical direction, from the top and the bottom) entering from channels 116, 117 at intersection 162. The intersection 162 leading into channel 164B is the second focusing region. Note that although the entrances into intersection 162 from channels 116, 117 are shown as rectangular, one of ordinary skill in the art would appreciate that any other suitable configuration (i.e., tapered, circular) may be used. The sheath or buffer fluids 163 in the channels 116, 117 (which may be disposed in different layers of the microfluidic chip 100 from channels 164A-B) enter at different planes into the channel 164A-B, to align the components 160 in the center of the channel 164B by both width and depth (i.e., horizontally and vertically) as they flow along channel 164B.

Thus, in one embodiment, with the second focusing step of the present invention, the sample mixture 120 is again compressed by the vertical sheath or buffer fluids 163 entering at channels 116, 117, and the sample 120 stream is focused at the center of the channel 164B depth, as illustrated in FIG. 5A, and the components 160 flow along the center of the channel 164B in approximately single file formation.

In one embodiment, the components 160 are sperm cells 160, and because of their pancake-type or flattened teardrop shaped head, the sperm cells 160 will re-orient themselves in a predetermined direction as they undergo the second focusing step—i.e., with their flat surfaces perpendicular to the direction of light beam 148 (see FIG. 5A). Thus, the sperm cells 160 develop a preference on their body orientation while passing through the two-step focusing process. Specifically, the sperm cells 160 tend to be more stable with their flat bodies perpendicular to the direction of the compression. Hence, with the control of the sheath or buffer fluids 163, the sperm cells 160 which start with random orientation, now achieve uniform orientation. Thus, the sperm cells 160 not only make a single file formation at the center of the channel 164B, but they also achieve a uniform orientation with their flat surface normal to the direction of compression in the second focusing step.

Thus, all components 160 introduced into sample input 106, which may be other types of cells or other materials as described above, etc., undergo the two-step focusing steps, which allow the components 160 to move through the channel 164B in a single file formation, in a more uniform orientation (depending on the type of components 160), which allows for easier interrogation of the components 160.

In one embodiment, further downstream in channel 164B, the components 160 are detected in the interrogation chamber 129 at opening 150 through coverings 132, 133, using the light source 147. Light source 147 emits a light beam 148 (which may be via an optical fiber) which is focused at the center of the channel 164C at opening 150. In one embodiment, the components 160, such as sperm cells 160, are oriented by the focusing streams (i.e., sheath or buffer fluid 163 streams which act on sample stream 120) such that the flat surfaces of the components 160 are facing toward the beam 148. In addition, all components 160 are moved into single file formation by focusing as they pass under beam 148. As the components 160 pass under light source 147 and are acted upon by beam 148, the components 160 emit the fluorescence which indicates the desired components 160. For example, with respect to sperm cells, X chromosome cells fluoresce at a different intensity from Y chromosome cells; or cells carrying one trait may fluoresce in a different intensity or wavelength from cells carrying a different set of traits. In addition, the components 160 can be viewed for shape, size, or any other distinguishing indicators.

In the embodiment of beam-induced fluorescence, the emitted light beam 151 (in FIG. 3) is then collected by the objective lens 153, and subsequently converted to an electronic signal by the optical sensor 154. The electronic signal is then digitized by an analog-digital converter (ADC) 155 and sent to an electronic controller 156 for signal processing. The electronic controller can be any electronic processor with adequate processing power, such as a DSP, a Micro Controller Unit (MCU), a Field Programmable Gate Array (FPGA), or even a Central Processing Unit (CPU). In one embodiment, the DSP-based controller 156 monitors the electronic signal and may then trigger at least one actuator driver (i.e., 157a or 157b), to drive one of the two piezoelectric actuator assemblies (109, 110, or 219, 220—part of the respective piezoelectric actuator assemblies 109, 110, 209, 210) when a desired component 160 is detected. In another embodiment, the FPGA-based controller monitors the electronic signal and then either communicates with the DSP controller or acts independently to trigger at least one actuator driver (i.e., 157a or 157b), to drive one of the two piezoelectric actuator assemblies (109, 110, or 219, 220—part of the respective piezoelectric actuator assemblies 109,110, 209, 210) when a desired component 160 is detected.

Thus, in one embodiment, selected or desired components 160 in channel 164C in the interrogation chamber 129, are isolated by a jet stream of buffer or sheath fluids 163 from one of the jet channels 127, 128, depending on which output channel 140, 142 is desired for the selected component 160. In one exemplary embodiment, the electronic signal activates the driver to trigger external stacked piezoelectric actuator 219 (or activates driver 157a to trigger actuator 109), at the moment when the target or selected component 160 arrives at the cross-section point of the jet channels 127, 128 and the main channel 164C. This causes external stacked piezoelectric actuator assembly 209 (or 109) to contact the diaphragm 170 and push it, compressing jet chamber 130, and squeezing a strong jet of buffer or sheath fluids 163 from jet chamber 130 via jet channel 127, into the main channel 164C, which pushes the selected or desired component 160 into output channel 142. Note that, similarly to the performance of stacked external piezoelectric actuator assembly 209, the triggering of piezoelectric actuator assembly 210 (or 110), would push a desired component 160 into the output channel 140 on the opposite side from the jet 128.

Thus, sheath or buffer fluids 163 jetted from one of the jet channels 127, 128 divert target or selected components 160 from their ordinary paths in channel 164C, toward one of the selected or desired, respective output channels 140, 142, isolating those target components 160, and enriching the flows in those output channels 140, 142, and depleting the flow in the sample fluid 120 which continues straight out through output channel 141 with unselected components, if any. Thus, no triggering of the piezoelectric actuator assemblies 109, 110, means that the unselected components 160 in the fluid mixture 120 continue straight out through output channel 141.

In one embodiment, the isolated components 160 are collected from one of the first output 111, or the third output 113, using known methods in the art, for storing, for further separation, or for processing, such as cryopreservation. Of course, components 160 that were not isolated into outputs 111, 113, may also be collected from second output 112. Portions of the first, second, and third outputs 111-113 may be characterized electronically, to detect concentrations of components, pH measuring, cell counts, electrolyte concentration, etc.

In one embodiment, interrogation of the sample 120 containing components 160 (i.e., biological material), is accomplished by other methods. Thus, portions of, or outputs from, the microfluidic chip 100 may be inspected optically or visually. Overall, methods for interrogation may include direct visual imaging, such as with a camera, and may utilize direct bright-light imaging or fluorescent imaging; or, more sophisticated techniques may be used such as spectroscopy, transmission spectroscopy, spectral imaging, or scattering such as dynamic light scattering or diffusive wave spectroscopy.

In some cases, the optical interrogation region 129 may be used in conjunction with additives, such as chemicals which bind to or affect components of the sample mixture 120 or beads which are functionalized to bind and/or fluoresce in the presence of certain materials or diseases. These techniques may be used to measure cell concentrations, to detect disease, or to detect other parameters which characterize the components 160.

However, in another embodiment, if fluorescence is not used, then polarized light back scattering methods may also be used. Using spectroscopic methods, the components 160 are interrogated as described above. The spectrum of those components 160 which had positive results and fluoresced (i.e., those components 160 which reacted with a label) are identified for separation by the activation of the piezoelectric assemblies 109, 110, 209, 210.

In one embodiment, the components 160 may be identified based on the reaction or binding of the components with additives or sheath or buffer fluids 163, or by using the natural fluorescence of the components 160, or the fluorescence of a substance associated with the component 160, as an identity tag or background tag, or met a selected size, dimension, or surface feature, etc., are selected for separation.

In one embodiment, upon completion of an assay, selection may be made, via computer 182 (which monitors the electronic signal and triggers the piezoelectric assemblies 109, 110, 209, 210) and/or operator, of which components 160 to discard and which to collect.

In one embodiment, the user interface of the computer system 182 includes a computer screen which displays the components 160 in a field of view acquired by a CCD camera 183 over the microfluidic chip 100.

In one embodiment, the computer 182 controls any external devices such as pumps (i.e., pumping mechanism of FIG. 9), if used, to pump any sample fluids 120, sheath or buffer fluids 163 into the microfluidic chip 100, and also controls any heating devices which set the temperature of the fluids 120, 163 being inputted into the microfluidic chip 100.

Chip Cassette and Holder

The microfluidic chip 100 is loaded on a chip cassette 212, which is mounted on chip holder 200. The chip holder 200 is mounted to a translation stage (not shown) to allow fine positioning of the holder 200. The microfluidic chip holder 200 is configured to hold the microfluidic chip 100 in a position such that the light beam 148 may intercept the components 160 in the above described manner, at opening 150. When the microfluidic chip 100 is in the closed position, a gasket layer 105 (see FIG. 1) forms a substantially leak-free seal between the main body 211 and the microfluidic chip 100.

As illustrated in FIG. 6, in one embodiment, a microfluidic chip holder 200 is made of a suitable material, such as aluminum alloy, or other suitable metallic/polymer material, and includes a main body 211, and at least one stacked external piezoelectric actuator 209, 210.

The main body 211 of the holder 200 may be any suitable shape, but its configuration depends on the layout of the chip 100. For example, the stacked external piezoelectric actuators 209, 210 must be placed over the diaphragm(s) 170, 171, such that contact is made between a tip of the piezoelectric actuator 219, 220 and the diaphragm 170, 171 of the microfluidic chip 100. The main body 211 of the holder 200 is configured to receive and engage with external tubing (see FIG. 9) for communicating fluids/samples to the microfluidic chip 100.

The details of these cassette 212 and holder 200 and the mechanisms for attachment of the chip 100 to the cassette 212 and holder 200, are not described in any detail, as one of ordinary skill in the art would know that these devices are well-known and may be of any configuration to accommodate the microfluidic chip 100, as long as the objectives of the present invention are met.

Figure 9:
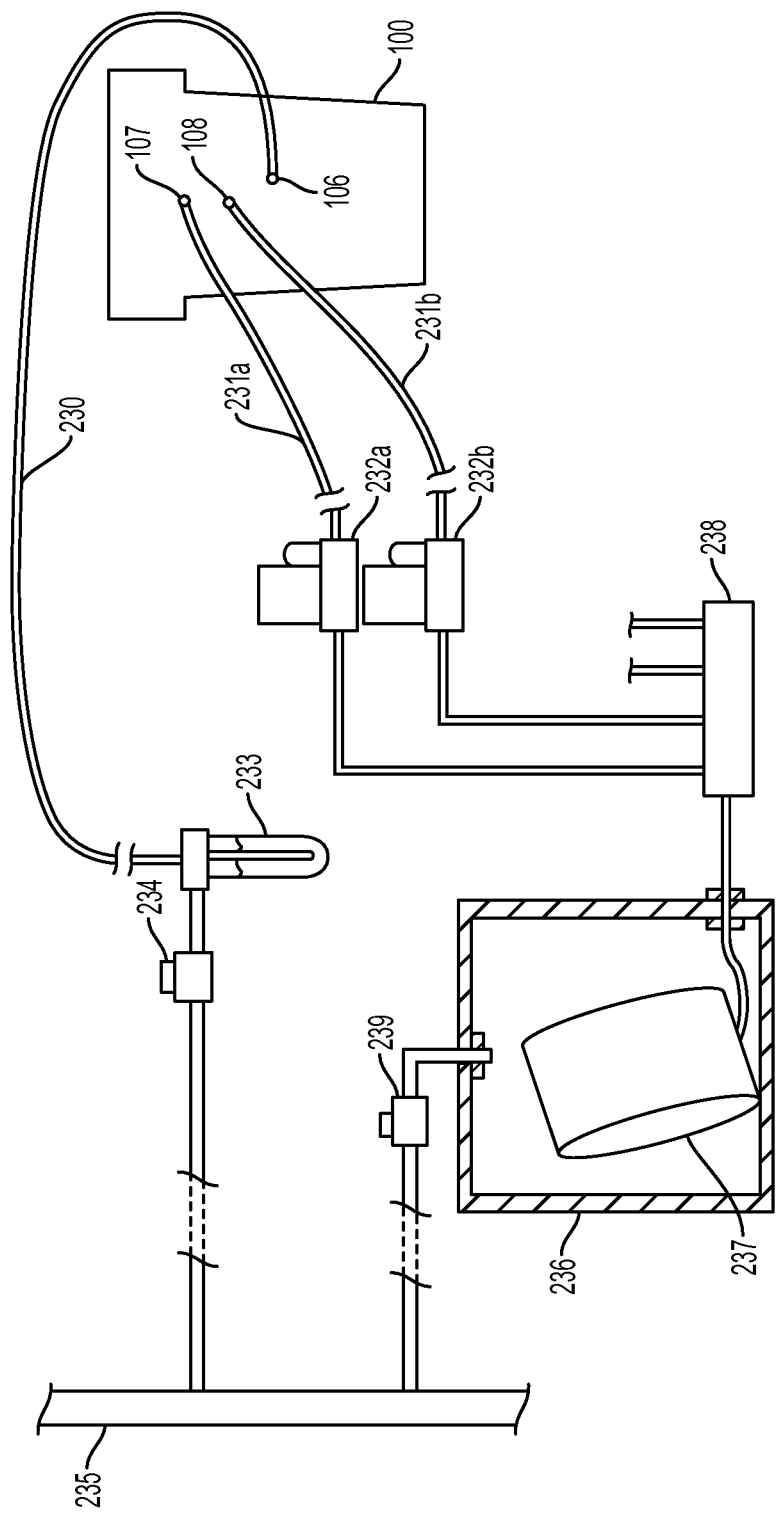
FIG. 9 shows a pumping mechanism which pumps sample fluid and sheath or buffer fluids into the microfluidic chip, according to one embodiment consistent with the present invention.

As shown in FIG. 9, in one embodiment, a pumping mechanism includes a system having a pressurized gas 235 which provides pressure for pumping sample fluid mixture 120 from reservoir 233 (i.e., sample tube) into sample input 106 of the chip 100.

A collapsible container 237 having sheath or buffer fluid 163 therein, is disposed in a pressurized vessel 236, and the pressurized gas 235 pushes fluid 163 to a manifold 238 having a plurality of different outputs, such that fluid 163 is delivered via tubing 231a, 231b to the sheath or buffer inputs 107, 108, respectively, of the chip 100.

A pressure regulator 234 regulates the pressure of gas 235 within the reservoir 233, and a pressure regulator 239 regulates the pressure of gas 235 within the vessel 236. A mass flow regulator 232a, 232b controls the fluid 163 pumped via tubing 231a, 231b, respectively, into the sheath or buffer inputs 107, 108, respectively. Thus, tubing 230, 231a, 231b is used in the initial loading of the fluids 120 into the chip 100, and may be used throughout chip 100 to load sample fluid 120 into sample input 106, or sheath or buffer inputs 107, 108. In addition, in one embodiment, tubing (not shown) can provide fluid 163 from manifold 238 into air vents 121, 122 to fill chambers 130, 131, for example.

In accordance with an illustrative embodiment, any of the operations, steps, control options, etc. may be implemented by instructions that are stored on a computer-readable medium such as a computer memory, database, etc. Upon execution of the instructions stored on the computer-readable medium, the instructions can cause a computing device to perform any of the operations, steps, control options, etc. described herein.

The operations described in this specification may be implemented as operations performed by a data processing apparatus or processing circuit on data stored on one or more computer-readable storage devices or received from other sources. A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network. Processing circuits suitable for the execution of a computer program include, by way of example, both general and special purpose microprocessors, and any one or more processors of any kind of digital computer.

It should be noted that the orientation of various elements may differ according to other illustrative embodiments, and that such variations are intended to be encompassed by the present disclosure.

The construction and arrangements of the microfluidic chip, as shown in the various illustrative embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various illustrative embodiments without departing from the scope of the present disclosure.

What is claimed is:

1. A microfluidic chip including a plurality of layers in which are disposed a plurality of channels, comprising:
    a sample input channel into which a sample fluid mixture of components to be isolated is inputted;
    a first plurality of sheath fluid channels into which sheath fluids are inputted, the first plurality of sheath fluid channels which intersect the sample input channel at a first intersection, such that the sheath fluids compress the sample fluid mixture on at least two sides, such that the sample fluid mixture becomes a relatively smaller, narrower stream, bounded by the sheath fluids, while maintaining laminar flow in the sample input channel;
    a second plurality of sheath fluid channels, substantially of the same dimensions as the first plurality of sheath fluid channels, into which sheath fluids are inputted, the second plurality of sheath fluid channels which intersect the sample input channel at a second intersection downstream from the first intersection, in a second direction substantially 90 degrees above and below the sample input channel, such that the sheath fluids from the second plurality of sheath fluid channels compress the sample fluid mixture, such that the components in the sample fluid mixture are compressed and oriented in a predetermined direction, while still maintaining laminar flow in the sample input channel; and
    a plurality of output channels stemming from the sample input channel, the plurality of output channels which removes the components and the sheath fluids from the microfluidic chip and
    at least one jet chamber containing sheath fluids introduced into said jet chamber by at least one air vent; and
    a diaphragm which covers each said jet chamber; and
    wherein an external, stacked piezoelectric actuator assembly aligns with and displaces said diaphragm, to drive said sheath fluids in said jet chamber into said sample input channel, to displace said trajectory of said stream of said sample fluid mixture in said sample input channel into one of said plurality of output channels.

2. The microfluidic chip according to claim 1, further comprising:
    an interrogation apparatus which interrogates and identifies said components in said sample fluid mixture in said sample input channel, in an interrogation chamber disposed downstream from said second intersection.

3. The microfluidic chip according to claim 2, further comprising:
    at least one jet channel which is connected to said at least one jet chamber, said at least one jet channel which enters said sample input channel at said interrogation chamber.

4. The microfluidic chip according to claim 1, wherein said external, stacked piezoelectric actuator assembly is disposed in a microfluidic chip holder.

5. The microfluidic chip according to claim 1, further comprising:
    an electronic circuit connected to said piezoelectric actuator assembly, said electronic circuit which amplifies an electronic signal generated by a resistance force from said piezoelectric actuator being in contact with said diaphragm.

6. The microfluidic chip according to claim 5, wherein an electric signal from said piezoelectric film shows how much of said strain is generated by said external, stacked piezoelectric actuator assembly.

7. The microfluidic chip according to claim 5, wherein an indicator of contact is turned on automatically when contact between said piezoelectric actuator and said diaphragm is made.

8. The microfluidic chip according to claim 7, wherein when said electronic signal exceeds a set threshold, it activates said indicator.

9. The microfluidic chip according to claim 8, wherein said indicator of contact includes a light, a sound, a haptic, or any combination thereof.

10. The microfluidic chip according to claim 1, wherein said piezoelectric actuator assembly includes:
    a flexible diaphragm which covers said jet chamber; and
    a piezoelectric material bonded on a top surface of said diaphragm by an adhering mechanism.

11. The microfluidic chip according to claim 10, wherein when voltage is applied across electrodes of said piezoelectric actuator assembly, said flexible diaphragm bends into said jet chamber and squeezes said sheath fluids from said jet chamber into said sample input channel to deflect said selected components into one of said plurality of output channels.

12. The microfluidic chip according to claim 3, wherein said jet channel is tapered when it connects to said sample input channel.

13. The microfluidic chip according to claim 1, further comprising:
a plurality of outputs disposed at ends of said plurality of output channels.

14. The microfluidic chip according to claim 13, wherein said plurality of output channels increase in dimension from said sample input channel.

15. The microfluidic chip according to claim 14, further comprising:
a plurality of notches disposed at a bottom edge of the microfluidic chip to isolate said plurality of outputs.

16. The microfluidic chip according to claim 2, wherein said sample input channel and said plurality of sheath channels are disposed in one or more planes of the microfluidic chip.

17. The microfluidic chip according to claim 2, wherein said sample input channel and said plurality of sheath channels are disposed in one or more structural layers, or in-between structural layers of the microfluidic chip.

18. The microfluidic chip according to claim 16, wherein at least one of said plurality of sheath channels is disposed in a different plane than a plane in which said sample input channel is disposed.

19. The microfluidic chip according to claim 17, wherein at least one of said plurality of sheath channels is disposed in a different structural layer than a structural layer in which said sample input channel is disposed.

20. The microfluidic chip according to claim 1, wherein said sample input channel tapers at an entry point into said first intersection with said plurality of sheath channels.

21. The microfluidic chip according to claim 2, wherein said sample input channel tapers into said interrogation chamber.

22. The microfluidic chip according to claim 1, wherein said plurality of sheath fluid channels taper at entry points into said sample input channel at least one of said first intersection or said second intersection.

23. The microfluidic chip according to claim 17, wherein said interrogation chamber includes an opening cut through said structural layers in the microfluidic chip; and
wherein a top window is configured to receive a first covering in an opening in at least one layer of said structural layers; and
a bottom window is configured to receive a second covering in an opening in at least one layer of said structural layers.

24. The microfluidic chip according to claim 16, wherein said interrogation chamber includes an opening cut through said planes in the microfluidic chip; and
wherein a top window is configured to receive a first covering in an opening in at least one plane of said planes of the microfluidic chip; and
a bottom window is configured to receive a second covering in an opening in at least one plane of said planes of the microfluidic chip.

25. The microfluidic chip according to claim 2, wherein said interrogation apparatus includes a light source configured to emit a beam through a first covering, to illuminate and excite said components in said sample fluid mixture; and
wherein emitted light induced by said beam passes through a second covering and is received by an objective lens.

26. The microfluidic chip according to claim 23, wherein said interrogation apparatus includes a light source configured to emit a beam through structural layers of the microfluidic chip, to illuminate and excite said components in said sample fluid mixture; and
wherein emitted light induced by said beam is received by an objective lens.

27. The microfluidic chip according to claim 24, wherein said interrogation apparatus includes a light source configured to emit a beam through said planes of the microfluidic chip, to illuminate and excite said components in said sample fluid mixture; and
wherein emitted light induced by said beam is received by an objective lens.

28. The microfluidic chip according to claim 26, wherein said emitted light received by said objective lens is converted into an electronic signal which triggers said piezoelectric actuator assembly.

29. The microfluidic chip according to claim 27, wherein said emitted light received by said objective lens is converted into an electronic signal which triggers said piezoelectric actuator assembly.

30. The microfluidic chip according to claim 1, wherein one of said sample fluid mixture or said sheath fluids is pumped into the microfluidic chip by a pumping apparatus.

31. The microfluidic chip according to claim 1, wherein external tubing communicates fluids to the microfluidic chip.

32. The microfluidic chip according to claim 1, wherein said components are cells.

33. The microfluidic chip according to claim 32, wherein the cells to be isolated include at least one of viable and motile sperm from non-viable or non-motile sperm; sperm isolated by gender and other sex sorting variations; stem cells isolated from cells in a population; one or more labeled cells isolated from un-labeled cells including sperm cells; cells, including sperm cells, distinguished by desirable or undesirable traits; genes isolated in nuclear DNA according to a specified characteristic; cells isolated based on surface markers; cells isolated based on membrane integrity or viability; cells isolated based on potential or predicted reproductive status; cells isolated based on an ability to survive freezing; cells isolated from contaminants or debris; healthy cells isolated from damaged cells; red blood cells isolated from white blood cells and platelets in a plasma mixture; or any cells isolated from any other cellular components into corresponding fractions.

34. The microfluidic chip according to claim 1, wherein said isolated components are moved into one of said plurality of output channels, and unselected components flow out through another of said plurality of output channels.

35. The microfluidic chip according to claim 30, further comprising:
a computer which controls said pumping of said one of said sample fluid mixture or said sheath fluids into the microfluidic chip.

36. The microfluidic chip according to claims 23, further comprising:
a computer which displays said components in a field of view acquired by a CCD camera disposed over said opening in the microfluidic chip.

37. The microfluidic chip according to claims 24, further comprising:
a computer which displays said components in a field of view acquired by a CCD camera disposed over said opening in the microfluidic chip.

* * * * *